(12) United States Patent
Roullet et al.

(10) Patent No.: US 10,201,510 B2
(45) Date of Patent: Feb. 12, 2019

(54) COMPOSITIONS AND METHODS FOR TREATMENT OF NEUROLOGICAL SYMPTOMS ASSOCIATED WITH ALCOHOL-WITHDRAWAL AND FOR CONVULSIVE SEIZURE

(75) Inventors: Jean-Baptiste Roullet, Portland, OR (US); John C. Crabbe, Jr., Portland, OR (US); Pamela Metten, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 809 days.

(21) Appl. No.: 11/815,513

(22) PCT Filed: Feb. 6, 2006

(86) PCT No.: PCT/US2006/004265
§ 371 (c)(1),
(2), (4) Date: May 28, 2008

(87) PCT Pub. No.: WO2006/086372
PCT Pub. Date: Aug. 17, 2006

(65) Prior Publication Data
US 2008/0286209 A1    Nov. 20, 2008

Related U.S. Application Data

(60) Provisional application No. 60/650,299, filed on Feb. 5, 2005, provisional application No. 60/650,301, filed on Feb. 5, 2005.

(51) Int. Cl.
| | | |
|---|---|---|
| *A61P 25/30* | (2006.01) | |
| *A61P 25/08* | (2006.01) | |
| *A61K 31/137* | (2006.01) | |
| *A61K 8/34* | (2006.01) | |
| *A61K 31/045* | (2006.01) | |

(52) U.S. Cl.
CPC .................... *A61K 31/137* (2013.01)

(58) Field of Classification Search
USPC ................. 424/45; 514/739, 671, 720, 725
See application file for complete search history.

(56) References Cited

U.S. PATENT DOCUMENTS 6,437,003 B1 * 8/2002 Roullet et al. ............... 514/725

OTHER PUBLICATIONS

Brahma et al., Structural Characteristics of Synthetic Retinoids, Methods in Enzymology, vol. 189, 1990, pp. 43-50.*
Altamura AC, Regazzetti MG, Porta M. Nimodipine in human alcohol withdrawal syndrome—an open study. *Eur Neuropsychopharmacol* 1990;1:37-40.
Banger M, Benkert 0, Roselle J, Herth T, Hebenstreit M, Philipp M, Aldenhoff JD. Nimodipine in acute alcohol withdrawal state. *J Psychiatric Res* 1992;26:117-123.
Bayard M, McIntyre J, Hill K, Woodside J. Alcohol withdrawal syndrome. *Am Fam Physician* 2004;69:1443-50.
Bentinger M, Grunler J, Peterson E, Swiezewska E, Daffier G. Phosphorylation of farnesol in rat liver microsomes: properties of farnesol kinase and farnesyl phosphate kinase. *Arch Biochem Biophys* 1997053:191-198.
Binet L, Binet P, Miocque M, Morin H, Pechery•C, Roux M. Le farnesol, substance psycho-sedative et spasmolytique. *Therapie* 1972;27:893-905.
Binet L, Binet P, Miocque M, Roux M, Bernier A. Recherche sur les proprietes pharmacodynamiques (action sedative et action spasmolytique) de quelques alcohols terpeniques aliphatiques. *Annales Pharmaceutiques Frangaise* 1972;30:611-616.
Binet P, Miocque M, Roux M, Rinjard P. Famesol et neuroleptiques. I. Renforcement par le famesol de l'effet cataleptigene experimental des neuroleptiques. *Annales Pharmaceutiques Francaise* 1975;33:229-234.
Binet P, Miocque M, Roux M, Rinjard P. Famesol et neuroleptiques. II. Action du farnesol, seul ou associó a un neuroleptique, sur les stereotypies provoquees chez le Rat par l'amphetamine. *Annales Pharmaceutiques Francaise* 1975;33:321-328.
Binet P. Action quelques alcohols terpeniques sur le systeme nerveux des poissons. *Annales Pharmaceutiques Frangaise* 1972;30:653-658.
Bone GH, Majchrowicz E, Martin PR, Linnoila M, Nutt DJ. A comparison of calcium. antagonists and diazepam in reducing ethanol withdrawal tremors. *Psychopharmacology* 1989;99:386-388.
Brennan CH, Crabbe J, Littleton JM. Genetic regulation of dihydropyridine-sensitive calcium channels in brain may determine susceptibility to physical dependence on alcohol. *Neuropharmacology* 1990;29:429-432.

(Continued)

*Primary Examiner* — Robert T. Crow
*Assistant Examiner* — John P Nguyen
(74) *Attorney, Agent, or Firm* — Whitham & Cook, P.C.

(57) ABSTRACT

Particular aspects of the present invention provide pharmaceutical compositions comprising isoprenoid-based compounds (e.g., farnesol and/or farnesol analogs or derivatives) or dehydroisoprenoid-based compounds, and novel methods for using same in treating (e.g., suppressing): alcohol withdrawal syndrome and associated neurological symptoms (e.g., depression, tremor, anxiety, autonomic hyperactivity (e.g., sweating, increased blood pressure, tachycardia), hallucinations, alcohol withdrawal seizures, delirium tremens (DT), and memory loss); or for treating in treating convulsive seizure (e.g., epileptic seizure, etc.). Particular pharmaceutical compositions and methods comprise the use of at least one compound selected from the group consisting of: (2E,6E)-3,7,11-trimethyldodeca-2,6,10-trien-1-ol (all-trans farnesol); (2Z,6E)-3,7,11-trimethyldodeca-2,6,10-trien-1-ol (cis-farnesol); (E)-3,7,11-trimethyldodeca-1,6,10-trien-3-ol nerolidol); (2E,6E)-3,7,11-trimethyldodeca-2,6,10-trien-1-amine (farnesylamine); (E)-3-(3,7-dimethylocta-2,6-dienyloxy)phenol (geranylresorcinol); (2E,6E)-,7,11-dimethyl-3-(trifluoromethyl)dodeca-2,6,10-trien-1-ol
(trifluorofarnesol); and (2E,4E,6E,8E)-3,7-dimethyl-9-(2,6,6-trimethylcyclohex-1-enyl)nona-2,4,6,8-tetraen-1-ol (all-trans retinol). According to additional aspects, compounds that target and inhibit enzymes that degrade/metabolize/inactivate the disclosed compounds have utility to induce endogenous accumulation thereof to suppress/prevent, e.g., alcohol withdrawal seizures or convulsive seizures.

21 Claims, 6 Drawing Sheets

(56) References Cited

OTHER PUBLICATIONS

Brennan Cl1, Littleton JM. Chronic exposure to anxiolytic drugs, working by different mechanisms causes up-regulation of dihydropyridine binding sites on cultured bovine adrenal chromaffin cells. Neuropharmacology 1991;30:199-205.

Bunk K, Metten P, Belknap J, Crabbe J. Quantitative trait loci affecting risk for pentobarbital withdrawal map near alcohol withdrawal loci on mouse chromosomes 1, 4, and 11. *Mammalian Genome* 1999;10:431-437.

Buck KJ, Metten P, Belknap JK, Crabbe JC. Quantitative trait loci involved in genetic predisposition to acute alcohol withdrawal in mice. *J Neuroscience* 1997;17:3946-3955.

Chang PH, Steinberg MB. Alcohol withdrawal. *Med Clin North Am* 2001;85:1191-1212.

Christopher J, Popjak G. Studies on the biosynthesis of cholesterol: XIV. The origin of prenoic acids from allyl pyrophosphates in liver enzyme systems. *J Lipid Res* 1961;2:244-257.

Crabbe JC, Young Jr. ER, Kosobud A (1983). Genetic correlations with ethanol withdrawal severity. *Phannacol Biochem Behav* 1983;18(Suppl. 1):541-547.

Crabbe JC. Sensitivity to ethanol in inbred mice: genotypic correlations among several behavioral responses. *Behav Neurosci* 1983;97:280-289.

Crabbe JC, Merrill C, Belknap JK. Acute dependence on depressant drugs is determined by common genes in mice. *JPharmacol Exp Ther* 1991;257:663-667.

Crabbe JC, Belknap JK, Buck KJ, Metten P. Use of recombinant inbred strains for studying genetic determinants of responses to alcohol. *Alcohol & Alcoholism* 1994;S2:67-71.

Crabbe JC, Belknap JK, Metten P, Grisel JE, Buck KJ. Quantitative trait loci: mapping drug and alcohol-related genes. *Adv Pharmacol* 1998;42:1033-1037.

Crabbe, J. C. (1998). "Provisional mapping of quantitative trait loci for chronic ethanol withdrawal severity in BXD recombinant inbred mice." *JPharmacol Exp Ther* 286(1):263-271.

Crews FT. Morrow AL. Criswell H. Breese G. Effects of ethanol on ion channels. *hit Rev Neurobiol* 1996;39:283-367.

Davies M. The role of GABAA receptors in mediating the effects of alcohol in the central nervous system. *J Psychiatr Neurosci* 2003;28:263-274.

DeLima JG, Xue H, Phanouvong T, Colburn L, McCarron DA, Bennett WM, Roullet J-B. In vivo and in vitro effect of FK506 in rat and human arteries. *Kidney Int.*, 1999;55:1518-1527.

Diamond I, Gordon AS. Cellular and molecular neuroscience of alcoholism. *Physiol. Rev.* 1997;77:1-20.

Dolence JM, Poulter CD. Synthesis of analogues of farnesyl diphosphate. *Tetrahedron* 1996;52:119-130.

Ertel EA, Campbell KP, Harpold MM, Hofmann F, Mori Y, Perez-Reyes E, Schwartz A, Snutch TP, Tanabe T, Birnbaumer L, Tsien RW, Catterail WA. Nomenclature of voltage-gated calcium channels. *Neuron* 2000;25:533-535.

Fehr C, Shirley RL, Belknap JK, Crabbe JC, Buck KJ. Congenic mapping of alcohol and pentobarbital withdrawal liability loci to a <1 centimorgan interval of murine chromosome 4: identification of Mpdz as a candidate gene. *J Neuroscience* 2002;22:3730-3738.

Goldstein DB. An animal model for testing effects of drugs on alcohol withdrawal reactions. *JPharmacol Exp Ther* 1972;183:14-22.

Grynkiewicz, G, Poenie M, Tsien RY. A new generation of $Ca^{2+}$ indicators with greatly improved fluorescence properties. *J Biol Chem* 1985;260:3440-3450.

Guppy LJ, Crabbe IC, Littleton JM. Time course and genetic variation in the regulation of calcium channel antagonist binding sites in rodent tissues during the induction of ethanol physical dependence and withdrawal. Alcohol Alcoholism 1995;30:607-615.

Hall AC, Lieb, WR, Franks NP. Insensitivity of P-type calcium channels to inhalational and intravenous general anesthetics. *Anesthesiology* 1994;81:117-123.

Han CL, Liao C-S, Wu C-W, Hwong CL, Lee AR, Yin SI Contribution to first-pass metabolism of ethanol and inhibition by ethanol for retinol oxidation in the human alcohol dehydrogenase family. *Eur. J. Biochem.* 1998;254:25-31.

Harper IC, Brennan CH, Littleton JM. Genetic up-regulation of calcium channels in a cellular model of ethanol dependence. Neuropharmacology 1989;28:1299-1302.

Hell TW. Westenbroek RE. Warner C. Ahlijanian MK. Prystay W. Gilbert MM. Snutch TP. Catterall WA. Identification and differential subcellular locaii7ation of the neuronal class C and class D L-type calcium channel alpha 1 subunits. *J Cell Biol* 1993;123:949-962.

Hoffman PL. NMDA receptors in alcoholism. *Int Rev Neurobiol* 2003;56:35-82.

Keung W-M. Human liver alcohol dehydrogenases catalyze the oxidation of the intermediary alcohols of the shunt pathway of mevilonate metabolism. *Biochem. Biophys. Res. Commun.* 1991;174:701-707.

Kosobud AE, Crabbe IC. Genetic influences on the development of alcohol physical dependence and withdrawal. In *The Genetics of Alcoholism* (Eds: H Begleiter and B Kissin), 221-256. Oxford University Press, Oxford, United Kingdom, 1995.

Lipscombe D. Pan JQ. Gray AC. Functional diversity in neuronal voltage-gated calcium channels by alternative splicing of Ca(v)alpha1. *Mol Neurobiol* 2002;26:21-44.

Linen RZ, Allen JP. Pharmacotherapies for alcoholism: promising agents and clinical issues. *Alcohol Clin Exp Res* 1991;15:620-633.

Little HI, Dolin SJ, Hlasey MI. Calcium antagonists decrease the ethanol withdrawal syndrome. *Life Sci* 1986;39:2059-2065.

Littleton JM, Little Hi, Whittington MA. Effects of dihydropyridine calcium channel antagonists in ethanol withdrawal: doses required, stereospecificity and actions of Bay K 8644. *Psychopharmacology* 1990;100:387-392.

Luft U, Bychkov R, Gollasch M, Gross V, Roullet J-B, McCarron DA, Ried C, Hoftnann F, Yagil Y, Yagil C, Haller H, Luft FC. Farnesol blocks the L-type $Ca^{2+}$ channel by targeting the $\square_1 c$ subunit. *Arterioscler Thromb Vasc Biol* 1999;19:959-966.

Mayo-Smith MF, Cushman P, Hill AJ, Jara G, Kasser C, Kraus M, Nauts D, Saitz R, Smith JW, Sulliva I, Thiessen N. Pharmacological management of alcogol withdrawal: a meta-analysis and evidence-based practice guideline. *JAMA* 1997;278:144-151.

McMahon T, Andersen R, Metten P, Crabbe JC, Messing RO. Protein kinase C $\square$ mediates up-regulation of N-type calcium channels by ethanol. *Mol Phannacol* 2000;57:53-58.

Messing RO, Carpenter CL, Diamond I, Greenberg DA. Ethanol regulates calcium channels in clonal neural cells. *Proc Natl Acad Sci USA*, 1989;83:6213-6215.

Metten P, Crabbe JC. Common genetic determinants of severity of acute withdrawal from ethanol, pentobarbital, and diazepam in inbred mice. *Behavioural Pharmacology* 1994;5:533-547.

Metten P, Crabbe JC. Dependence and Withdrawal. In *Pharmacological Effects of Ethanol on the Central Nervous System*. R.A. Deitrich and V. G. Erwin, Editors. CRC Press, Boca Raton, FL, CRC Press, pp. 269-290, 1996.

Metten P, Belknap IK, Crabbe JC. (1998). "Drug withdrawal convulsions and susceptibility to convulsants after short-term selective breeding for acute ethanol withdrawal." *Behav Brain Res* 1998;95:113-22.

Metten P, Crabbe JC. Genetic determinants of severity of acute withdrawal from diazepam in mice: commonality with ethanol and pentobarbital. *Phannacol Biochem Behav* 1999;63:473-479.

Mohri Y, Katsura M, Shuto K, Tsujimura A, Ishii R, Obkuma S. L-type high voltage-gated calcium channels cause an increase in diazepam binding inhibitor mRNA expression after sustained exposure to ethanol in mouse cerebral cortical neurons. Brain Res Mol Brain Res 2003;113:52-56.

Moreno Davila H. Molecular and functional diversity of voltage-gated calcium channels. *Annals of the New York Academy of Sciences*. 868:102-17, Apr. 30, 1999.

Mullikin-Kilpatrick D, Mehta ND, Hildebrandt JD, Treistman SN. Gi is involved in ethanol inhibition of L-type calcium channels in undifferentiated but not differentiated PC-12 cells. *Mol Pharmacol* 1995;47: 997-1005.

Myrick H, Anton RF. Treatment of alcohol withdrawal. *Alcohol Health Res World* 1998;22:38-43.

(56) References Cited

OTHER PUBLICATIONS

NGouemo P, Morad M. Ethanol withdrawal seizure susceptibility is associated with upregulation of L- and P-type $Ca^{i*}$ channel current in rat inferior colliculus neurons. Neurophannacology 2003;45:429-437.

Roullet J-B, Xue H, Pappu AS, Roullet C, Holcomb S, McCarron DA. Mevalonate availability and cardiovascular functions. *Proc Nati Acad Sci, USA* 1993;90:11728-11732.

Roullet J-B, Xue H, Roullet CH, Fletcher WS, Cipolla MJ, Harker CT, MCarron DA. Mevalonate availability affects human and rat resistance vessel function. *J Clin Invest* 1995; 96:239-244.

Roullet J-B, Xue H, Chapman J, McDougal P, Roullet CM, McCarron DA. Farnesyl analogues inhibit vasoconstriction in animal and human arteries. *J Clin Invest* 1996;97:23842390.

Roullet J-B, Le Quan Sang KH, Luft U, McCarron DA, Devynck MA. Farnesol, a potent inhibitor of vasoconstriction, decreases vascular smooth muscle cell $Ca^{2+}$ uptake without affecting membrane fluidity. *J Hypertens* 1997a;15:1723-1728.

Roullet J-B, Luft UC, Xue H, Chapman J, Bychov R, Roullet CM, Luft FC, Haller H, McCarron DA. Farnesol inhibits L-type $Ca^{2+}$ channels in vascular smooth muscle cells. *J Biol Chem* 199'7b;272:32240-32246.

Roullet J-B, Spaetgens RL, Burlingame T, Zamponi GW. Modulation of presynaptic calcium channels by the mevalonate pathway. *J Biol Chem,* 1999;274:25439-25446.

Saitz R, O'Malley SS. Pharmacotherapies for alcohol abuse. Withdrawal and treatment. *Medical Clinics of North America* 1997;81:881-907.

Sen SE, Roach S. A convenient two-step procedure for the synthesis of allylic amines from alcohols. *Synthesis* 1995:756-758.

Shulman A, Jagoda J, Laycock G, Kelly H. Calcium channel blocking drugs in the management of drug dependence, withdrawal and craving. A clinical pilot study with nifedipine and verapamil. *Australian Family Physician* 1998;27:S19-24.

Solem M, McMahon T, Messing RO. Protein kinase A regulates the inhibition of N- and P/Q-type calcium channels by ethanol in PC12 cells. *J Pharmacol Exp Ther,* 1997;282:14871495.

Victor M, Brausch C. The role of abstinence in the genesis of alcoholic epilepsy. *Epilepsy* 1967;8:1-20.

Waller GR Dehydrogenation of trans,trans farnesol by horse liver alcohol dehydrogenase. *Nature* 1965;207;13894390.

Walter HJ, Messing RO. Regulation of neuronal voltage-gated calcium channels by ethanol. .*Neurochem Int* 1999;35:95-101.

Wang X, Lemos JR, Dayanthi G, Nordmann JJ, Treitsman SN. Ethanol reduces vasopressin release by inhibiting calcium currents in nerve terminals. *Brain Res* 1991;551:339-341.

Wang X-D. Chronic alcohol intake interferes with retinoid metabolism. and signaling. *Nutr Rev* 1998;57:51-59.

Watson WP. Little H.T. Selectivity of the protective effects of dihydropyridine calcium channel antagonists against the ethanol withdrawal syndrome. *Brain Res* 2002;930:111-122.

Westfall D, Aboushadi N, Shackelford JE, Krisans SK. Metabolism of farnesol: phosphorylation of farnesol by rat liver microsomal and peroxisomal fractions. *Biochem Biophys Res Commun* 1997;230:562-568.

Whittington MA, Little M. A calcium channel antagonist stereo selectively decreases ethanol withdrawal hyperexcitability but not that due to bicuculline, in hippocampal slices. *Br J Pharmacol* 1991a;103 :1313-1320.

Whittington MA, Dolin SJ, Patch TL, Siarey RJ, Butterworth AR, Little 1-1J. Chronic dihydropyridine treatment can reverse the behavioral consequences of and prevent adaptations to chronic ethanol treatment. *Br J Pharmacol* 1991b;103:1669-1676.

Whittington MA, Little HI Changes in voltage-operated calcium channels modify ethanol withdrawal hyperexcitability in mouse hippocampal slices. *Exper Physiol* 1993;78:347-370.

* cited by examiner

COMPOSITIONS AND METHODS FOR TREATMENT OF NEUROLOGICAL SYMPTOMS ASSOCIATED WITH ALCOHOL-WITHDRAWAL AND FOR CONVULSIVE SEIZURE

CROSS REFERENCE TO RELATED APPLICATIONS

This application claims the benefit of priority to International Application Serial Number PCT/US2006/04265, filed 6 Feb. 2006, U.S. Provisional Patent Application Ser. No. 60/650,299, filed 5 Feb. 2005, and to U.S. Provisional Patent Application Ser. No. 60/650,301, filed 5 Feb. 2005, all of which are incorporated by reference herein in their entirety.

FIELD OF THE INVENTION

Aspects of the present invention relate generally to alcohol withdrawal syndrome (AWS), and isoprenoid-based compounds, and more particularly to pharmaceutical compositions comprising calcium channel blockers (e.g., isoprenoids such as farnesol and/or farnesol analogues or derivatives, or dehydroisoprenoid-based compounds), and novel methods for using same in treating AWS and alcohol associated neurological symptoms including, but not limited to depression, tremor, anxiety, autonomic hyperactivity (e.g., sweating, increased blood pressure, tachycardia), hallucinations, alcohol withdrawal seizures, delirium tremens (DT), and memory loss. Additional aspects relate generally to convulsive seizure, and more particularly to pharmaceutical compositions comprising calcium channel blockers (e.g., isoprenoids such as farnesol and/or farnesol analogues or derivatives), and methods for using same in treating convulsive seizure (e.g., epileptic seizure, etc.) and related symptoms and conditions.

BACKGROUND

Alcohol Withdrawal Symptoms.

In alcohol-dependent persons, cessation of drinking may lead to craving for alcohol and symptoms of alcohol withdrawal syndrome (AWS) (Victor, 1967, Chang, 2001, Bayard, 2004). These symptoms usually occur within 12 to 72 hours after the last drink and range in type, intensity, timing and frequency. The symptoms include tremor, anxiety, autonomic hyperactivity (sweating, increased blood pressure, tachycardia), hallucinations, seizures and delirium tremens (DT).

Alcohol Withdrawal Seizures.

Alcohol withdrawal (AW) seizures are considered a major AWS symptom together with DT and hallucinations. AW seizures are described as occurring in approximately 10% of people withdrawing from alcohol, being generalized tonic-clonic (95%), often multiple (60%), and usually occurring 7-48 hours after cessation of drinking (90%) (Victor, 1967). Most AW seizures are noted as having normal EEG (90%) and occurring within a period of 6 hours or less from first to last seizure (85% of patients). There is no reported gender or ethnic specificity of the seizures. The occurrence of AW seizures and DT in alcoholic patients requires immediate attention and treatment.

Pathophysiology of AWS and AW Seizures: Role of Ion Channels.

Chronic alcohol exposure is known to modify the neuronal expression of ion channels implicated in neurotransmission: ligand-activated, γ-aminobutyric (GABA)$_A$ and NMDA receptor-channels, and voltage-gated, L- and N-type Ca$^{2+}$ channels. The effect of chronic alcohol on ion channels varies depending on the type of channel but overall, it leads to a state of hyperexcitability of the central nervous system and accounts for much of the neurological symptoms associated with alcohol withdrawal.

Pathophysiology of AWS and AW Seizures: Role of Ion Channels.

Acutely, ethanol affects many of the ion channels implicated in neurotransmission and brain function: ligand-activated (GABA and glutamate) receptor/channels, and voltage-gated ion channels (L-, N- and P/Q type Ca$^{2+}$ channels). Chronically, ethanol leads to neuroadaptative changes in the activity and expression of these channels. It is currently believed that AW seizure is a manifestation of such changes, when ethanol is abruptly withdrawn (Crews, 1996; Metten, 1996).

Ligand-Gated Ion Channels—GABA and Glutamate Receptors.

Ethanol affects GABA-mediated neurotransmission and GABA receptors (Davies, 2003). Acutely, it enhances the stimulatory effect of GABA on GABA$_A$ receptors. In contrast, chronic exposure to alcohol modifies the subunit composition of the receptor and reduces the sensitivity of the channel to ethanol (Crews, 1996). It is believed that GABA$_A$ receptor stimulation contributes to the anxiolytic and sedative effect of ethanol whereas GABA$_A$ inhibition or desensitization to ethanol is anxiogenic and excitatory. The importance of GABA$_A$ receptors in the pathogenesis of AWS is underscored by the effectiveness of GABA$_A$ receptor agonists (e.g., benzodiazepines, barbiturates) in the treatment of AWS seizures.

Glutamate-activated receptors are excitatory, post-synaptic channels that are permeable to sodium and calcium. Their activation depolarizes the postsynaptic neuronal membrane and increases the probability of downstream firing. Acutely, ethanol antagonizes all three classes of glutamate receptors: N-methyl-D-aspartic acid (NMDA) receptors, AMPA and kainate receptors (Crews, 1996; Hoffman, 2003). In contrast, chronic exposure to ethanol leads to a compensatory increase in NMDA receptor expression and glutamate "supersensitivity." NMDA receptor up-regulation is considered a key component of alcohol withdrawal and also a major contributor to ethanol-induced, Ca$^{2+}$-mediated neuronal death. Thus the development of NMDA antagonists may be useful for reducing the acute symptoms of alcohol withdrawal as well as the excitotoxic brain damage associated with seizures, head trauma, and thiamine deficiency in alcoholics.

Voltage-Gated Ca$^{2+}$ Channels.

There are several types of voltage-gated Ca$^{2+}$ channels (Moreno, 2002; Lipscombe, 2002), all of which are sensitive to changes in membrane potential and allow calcium ions to flow in neurons when activated by action potentials. The channel-dependent calcium signals play a primary role in neurotransmitter release in the synaptic space, and also in the activation of intracellular calcium-sensitive processes. Three voltage-gated Ca$^{2+}$ channel types have been recognized as playing a major role in both acute and chronic alcohol toxicity: the L-, the N- and the P/Q types. L-type Ca$^{2+}$ channels are rather ubiquitously distributed in the CNS, and in many other tissues. In neurons, the L-type calcium channels are localized predominantly on cell bodies and proximal dendrites (Hell, 1993). They are thought to be involved in cell differentiation and gene activation, but have also been implicated in neurotransmission as indicated by the significant effect of L-type Ca$^{2+}$ channel agonists and antagonist on AWS and alcohol-withdrawal seizures. N- and P/Q type $Ca^{2+}$ channels are concentrated in presynaptic areas and play a significant role in the release of neurotransmitters from intracellular storage vesicles in the synaptic space.

L-Type $Ca^{2+}$ Channels.

Acute exposure to ethanol blocks L-type voltage-gated $Ca^{2+}$ channels. It is a slow-developing block with $IC_{50}$ ranging from 10-200 mM and characterized by a reduction in open probability of the channel and a small hyperpolarizing shift in the steady state inactivation of the channel (Mullikin-Kirkpatrick, 1995). As observed with NMDA receptors, chronic exposure to ethanol leads to compensatory upregulation of the expression of L-type $Ca^{2+}$ channels in the brain. This effect has been confirmed in many studies using tissue homogenates or hippocampal slices, and can be easily reproduced in vitro using PC12 cells (a clonal line of neural crest origin) cultured for several days in the presence of ethanol (Messing, 1986; Harper, 1989, Brennan, 1990 & 1991). The work by Guppy and colleagues (Guppy, 1995) is particularly interesting in that it shows that, in rats, alcohol-induced upregulation of the L-type channels (as determined by [$^3$H]nitrendipine binding) occurs as early as 3 days in the brain cortex and is reversible. The study also shows that, if channel expression returns to normal within 24 hours after withdrawal, it has only decreased by 50% when seizures are maximum (6-8 hours post withdrawal) and ethanol has disappeared from the circulation. Taken together, the data suggest that enhanced L-type $Ca^{2+}$ channel activity is a key factor in the onset of seizures in this model. Interestingly, there seems to be a relationship between genetic susceptibility to alcohol-induced seizures and genetic regulation of neuronal calcium channels in brain. Indeed, it was shown by Brennan and colleagues (Brennan, 1990) that mice selectively bred for severe withdrawal seizures (WSP) have a significantly greater up-regulation of brain L-type $Ca^{2+}$ channels (assessed as [$^3$H]nitrendipine binding sites) than mice resistant to withdrawal (WSR mice). Thus voltage-gated L-type $Ca^{2+}$ channels are intimately associated with the onset of alcohol-induced seizures and AWS-related hyperexcitability. The mechanism by which up-regulation of L-type $Ca^{2+}$ channels leads to hyperexcitability may simply be a direct increase in intraneuronal $Ca^{2+}$ availability followed by enhanced neurotransmitter release. However, a recent study showed that nifedipine blocks ethanol-induced increased message expression of DBI, a diazepam binding inhibitor that colocalizes with GABA in synaptic vesicles (Mohri, 2003). This finding suggests that L-type $Ca^{2+}$ channels may also contribute to hyperexcitability in AWS patients by secondarily decreasing GABAergic neurotransmission.

N- and P/Q Type $Ca^{2+}$ Channels.

Less is known about the effect of ethanol on N- and P/Q type voltage-gated $Ca^{2+}$ channels. However, a pattern similar to what has been reported for L-type voltage-gated $Ca^{2+}$ channels (acute inhibition, chronic upregulation) emerges from the few studies that have examined the issue. Wang et al. (Wang, 1991), using rat neurohypophysis preparations, reported an inhibitory effect of ethanol on N-type $Ca^{2+}$ channels. More recently, Solem and colleagues reported that ethanol inhibits N-type and P/Q-type $Ca^{2+}$ channel dependent $Ca^{2+}$ signaling in nerve growth-factor (NGF) treated PC12 cells (Solem, 1997). The effect of ethanol on P-type currents has not been consistently observed though, and in rat Purkinje neurons, P-type currents appear insensitive to ethanol (Hall, 1994). In contrast to its acute effect, chronic ethanol up-regulates N- and P-type $Ca^{2+}$ channels, both in vitro (PC12 cells, McMahon, 1999) and in vivo (mouse, McMahon, 1999; rat, N'Gouemo, 2003). Interestingly, the effect of ethanol on mouse brain (cortex, hippocampus) N-type $Ca^{2+}$ channels is significant after 3 days of exposure to ethanol, a time when animals are prone to seizures upon withdrawal (McMahon, 1999). Also, the effect of chronic ethanol on P-type $Ca^{2+}$ channels was demonstrated in the inferior colliculus, a part of the brain and neural network implicated in audiogenic seizures following ethanol withdrawal. Thus, both N- and P-type $Ca^{2+}$ channels play a significant role in the pathogenesis of AWS-related seizures and, like L-type $Ca^{2+}$ channels, they are putative molecular targets for anti-withdrawal medications.

Other Ion Channels.

Other ion channels including strychnine-sensitive glycine receptors, nicotinic receptor ion channels and 5-hydroxytryptamine receptor channels have been recognized as potential players in alcohol toxicity and may be implicated in AWS seizures. These channels too are putative targets for new AWS medications.

Current Treatments for AWS, and Limitations Thereof.

A number of drugs have been used in the treatment of AWS and related seizures: neuroleptic compounds, beta adrenergic antagonists, alpha adrenergic agonists (clonidine), carbamazepine, barbiturates. However, at this time the drugs of choice in the U.S. are the benzodiazepines (for review see Mayo-Smith, 1997; Saitz, 1997; and Myrick, 1998).

Some studies have demonstrated the efficacy of barbiturates in reducing signs and symptoms of withdrawal. Phenobarbital in particular, has well-documented anticonvulsive activity, can be administered by oral, intramuscular and intravenous routes and has a low abuse potential. However, like other barbiturates, it poses a risk of respiratory depression, particularly when combined with alcohol, and has an overall lower safety profile than benzodiazepines when used at high doses. Both benzodiazepines and barbiturates have been shown to exhibit cross-dependence with alcohol (in fact, that is why they work to suppress withdrawal) and are also abused by humans (Litten & Allen, 1991). Many lines of evidence suggest that some genes mediating withdrawal seizures from alcohol also mediate withdrawal from other central nervous system depressants (Metten, 1994, 1998, 1999; Buck, 1997, 1999; Fehr, 2002).

Beta-adrenergic antagonists may be useful in reducing the autonomic manifestations of withdrawal such as elevated blood pressure. However, there is no indication that these compounds are effective in reducing seizures during withdrawal. Further, these compounds are known to increase the risk for delirium.

Antiepileptic medications (e.g., carbamazepine and valproic acid) have been successfully used to treat alcohol withdrawal for many years in Europe. Carbamazepine in particular was found to be superior to barbiturate and oxazepam for patients with mild to moderate withdrawal, and thus may provide a reasonable alternative to benzodiazepines.

Neuroleptic agents, including phenothiazines and haloperidol show effectiveness in reducing certain signs and symptoms of withdrawal (hallucinations). However, they are less effective than benzodiazepines in preventing delirium tremens and seizures, and can induce epileptic seizures by decreasing seizure threshold.

Current Treatments for AWS, and Limitations Thereof.

A number of drugs have been used in the treatment of AWS and related seizures: neuroleptic compounds, beta adrenergic antagonists, alpha adrenergic agonists (clonidine), carbamazepine, barbiturates. However, at this time the drugs of choice in the U.S. are the benzodiazepines (for review see Mayo-Smith, 1997; Saitz, 1997; and Myrick, 1998).

Some studies have demonstrated the efficacy of barbiturates in reducing signs and symptoms of withdrawal. Phenobarbital in particular, has well-documented anticonvulsive activity, can be administered by oral, intramuscular and intravenous routes and has a low abuse potential. However, like other barbiturates, it poses a risk of respiratory depression, particularly when combined with alcohol, and has an overall lower safety profile than benzodiazepines when used at high doses. Both benzodiazepines and barbiturates have been shown to exhibit cross-dependence with alcohol (in fact, that is why they work to suppress withdrawal) and are also abused by humans (Litten & Allen, 1991). Many lines of evidence suggest that some genes mediating withdrawal seizures from alcohol also mediate withdrawal from other central nervous system depressants (Metten, 1994, 1998, 1999; Buck, 1997, 1999; Fehr, 2002).

Beta-adrenergic antagonists may be useful in reducing the autonomic manifestations of withdrawal such as elevated blood pressure. However, there is no indication that these compounds are effective in reducing seizures during withdrawal. Further, these compounds are known to increase the risk for delirium.

Antiepileptic medications (e.g., carbamazepine and valproic acid) have been successfully used to treat alcohol withdrawal for many years in Europe. Carbamazepine in particular was found to be superior to barbiturate and oxazepam for patients with mild to moderate withdrawal, and thus may provide a reasonable alternative to benzodiazepines.

Neuroleptic agents, including phenothiazines and haloperidol show effectiveness in reducing certain signs and symptoms of withdrawal (hallucinations). However, they are less effective than benzodiazepines in preventing delirium tremens and seizures, and can induce epileptic seizures by decreasing seizure threshold.

Currently, benzodiazepines, a class of compounds that activates GABA receptors are the recommended treatment of alcohol withdrawal particularly when associated with seizures. However, agents that target the other ion channels may also be useful as withdrawal-specific medications.

Therefore, while a limited number of drugs are currently available (e.g., benzodiazepines, antiepileptic and neuroleptic agents), current understanding of AWS pathophysiology suggests that signaling pathways not targeted by these drugs, but implicated in AWS, may also be legitimate targets for medication development to treat alcohol withdrawal.

As discussed above, chronic administration of ethanol induces upregulation of brain L-type $Ca^{2+}$ channels. These channels are the target of dihydropyridine L-type $Ca^{2+}$ channel antagonists, a class of compound used for the treatment of high blood pressure. Experimentally, calcium channel antagonists prevent ethanol-induced up-regulation of the L-type $Ca^{2+}$ channels (Brennan, 1990; Whittington, 1991a), and suppress the development of hippocampal hyperexcitability to ethanol (Whittington, 1991a,b). Other studies have shown that acute administration of nimodipine and nitrendipine block withdrawal seizures in the animal (Bone, 1989; Little, 1986; Littleton, 1990). More recently (Watson, 2002), it was shown that the antiseizure activity of $Ca^+$ channel antagonists were selective for alcohol withdrawal seizures (no prevention of bicuculline or pentylenetetrazol-induced convulsions). Collectively, however, while current animal data suggests that calcium channel antagonists may be useful in the treatment of AWS in humans, only a few clinical studies have been conducted, showing either a moderate beneficial effect (Altamura, 1990; Shulman 1998) or no effect (Banger, 1992). Thus, the efficacy of calcium channel blockers in treating AWS, remains to be confirmed in humans, and significantly, the dihydropyridine calcium channel antagonists used in the Altamura and Shulman studies, are very selective compounds that act exclusively on L-type $Ca^{2+}$ channels.

Therefore, there is a pronounced need in the art for more effective treatment of AWS in humans. It is possible that calcium channel blockers with a larger spectrum of activity (i.e., active on more than one class of voltage-gated $Ca^{2+}$ channels) would be more effective in the treatment of AWS.

Convulsive Seizure.

Periodic unpredictable occurrences of seizures are commonly associated with epilepsy. The two main types of epileptic seizures are partial seizures and generalized seizures.

Partial seizures are characterized as those that affect neurons limited to part of one cerebral hemisphere, and may be accompanied by impairment of consciousness.

Generalized seizures include those in which both hemispheres are involved and consciousness is usually impaired. Generalized seizures include absence seizures, myoclonic seizures, clonic seizures, tonic seizures, tonic-clonic seizures and atonic seizures (see, e.g., Dreifuss et al., Classification of Epileptic Seizures and the Epilepsies and Drugs of Choice for Their Treatment, p. 1-9, In: Antiepileptic Drugs: Pharmacology and Therapeutics, Eds M. J. Eadie and F. J. E. Vajda; Wilder et al., Classification of Epileptic Seizures, p. 1-13, In: Seizure Disorders, A Pharmacological Approach to Treatment, Raven Press, New York (1981); McNamara, Drugs Effective in the Therapy of Epilepsies, p. 476-486, In: Goodman & Gilman's The Pharmacological Basis of Therapeutics, $9^{th}$ ed., Eds P. B. Molinoff, R. W. Ruddon (1996)).

Pseudoepileptic or non-epileptic seizures can be caused by a definable medical condition, for example, cardiovascular disease including arrhythmias, aortic stenosis, severe hypertension and orthostatic hypotension; toxic or metabolic disorders including hypoglycemia and drug toxicity; or sleep disorders. Non-epileptic seizures can also be induced by psychiatric conditions, e.g., hysteria, schizophrenia.

Thus, convulsions or seizures can result from disorders or specific conditions, e.g., epilepsy, acquired immunodeficiency syndrome (AIDS), Parkinson's disease, Alzheimer's disease, other neurodegenerative disease including Huntington's chorea, schizophrenia, obsessive compulsive disorders, tinnitus, neuralgia, trigeminal neuralgia, post-traumatic epilepsy, intoxication or withdrawal from barbiturates, brain illness or injury, brain tumor, choking, drug abuse, electric shock, fever (especially in young children), head injury, heart disease, heat illness, high blood pressure, meningitis, poisoning, stroke, toxemia of pregnancy, uremia related to kidney failure, venomous bites and stings, withdrawal from benzodiazepines, febrile convulsions, and afebrile infantile convulsions.

Therefore, there is a pronounced need in the art for more effective treatment of not only of AWS in humans, but also of convulsive seizure. It is possible that calcium channel blockers with larger spectrum of activity (i.e., active on more than one class of voltage-gated $Ca^{2+}$ channels) would be more effective in the treatment of convulsive seizure.

SUMMARY OF THE INVENTION

According to particular aspects of the present invention, isoprenoid-based compounds that are calcium channel blockers with a broad spectrum of activity (i.e., active on more than one class of voltage-gated $Ca^{2+}$ channels) are surprisingly effective in the treatment of AWS.

According to additional aspects of the present invention, isoprenoid-based compounds that are calcium channel blockers with a broad spectrum of activity (i.e., active on more than one class of voltage-gated $Ca^{2+}$ channels) are surprisingly effective in the treatment of convulsive seizure.

Particular embodiments provide pharmaceutical compositions comprising isoprenoid-based compounds (e.g., farnesol and/or farnesol analogues or derivates, and including dehydroisoprenoid-based compounds), and methods for using same in treating alcohol withdrawal syndrome (AWS) and associated neurological symptoms including, but not limited to depression, tremor, anxiety, autonomic hyperactivity (e.g., sweating, increased blood pressure, tachycardia), hallucinations, seizures, delirium tremens (DT), and memory loss. Preferably, the inventive compositions and methods are for treatment (e.g., suppression) of alcohol withdrawal seizures. Preferably, the inventive compositions and methods are for prevention of alcohol withdrawal seizures.

Additional embodiments provide pharmaceutical compositions comprising isoprenoid-based compounds (e.g., farnesol and/or farnesol analogues or derivates, and including dehydroisoprenoid-based compounds), and methods for using same in treating convulsive seizure and related conditions. Preferably, the inventive compositions and methods are for treatment (e.g., suppression) of convulsive seizures. Preferably, the inventive compositions and methods are for prevention of convulsive seizures.

In particular aspects, the pharmaceutical compositions and methods, comprise the use of at least one compound selected from the group consisting of: (2E,6E)-3,7,11-trimethyldodeca-2,6,10-trien-1-ol (all-trans farnesol); (2Z,6E)-3,7,11-trimethyldodeca-2,6,10-trien-1-ol (cis-farnesol); (E)-3,7,11-trimethyldodeca-1,6,10-trien-3-ol (nerolidol); (2E,6E)-3,7,11-trimethyldodeca-2,6,10-trien-1-amine (farnesylamine); (E)-3-(3,7-dimethylocta-2,6-dienyloxy) phenol (geranylresorcinol); (2E,6E)-,7,11-dimethyl-3-(trifluoromethyl)dodeca-2,6,10-trien-1-ol (trifluorofarnesol); and (2E,4E,6E,8E)-3,7-dimethyl-9-(2,6,6-trimethylcyclohex-1-enyl)nona-2,4,6,8-tetraen-1-ol (all-trans retinol).

Preferably, the subject is human. In particular aspects, at least one of the inventive farnesol compound is administered from 1 to 3 times per day. Preferably, delivery is via intranasal delivery of at least one of an aerosolized composition, and a nebulized composition. In particular embodiments, administration is via pulmonary delivery. Preferably, pulmonary delivery is via intranasal delivery of at least one of an aerosolized composition, and a nebulized composition.

The disclosed compounds are surprisingly versatile and effective, based at least in part on their distinctive isoprenoide-based structures.

According to additional aspects of the invention, compounds that target and inhibit enzymes that degrade/metabolize/inactivate isoprenoid-based inventive compositions (e.g., farnesol and/or farnesol analogues or derivates, and including dehydroisoprenoid-based compounds) are used to induce endogenous accumulation of the disclosed compounds and suppress/prevent seizures.

DETAILED DESCRIPTION OF THE INVENTION

Figure 1:
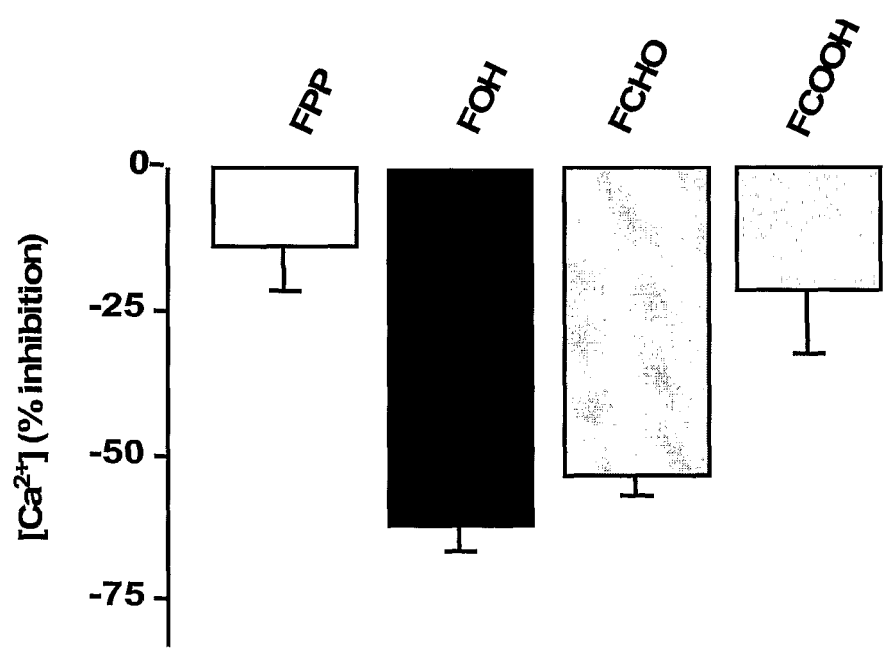
FIG. 1 shows results of an investigation of the activity of farnesol metabolites on neuronal voltage-gated L-type $Ca^{2+}$ channels. The $Ca^{2+}$ channel activity is expressed as % inhibition of KCl-induced intracellular $Ca^{2+}$ signaling in non-NGF differentiated PC12 cells loaded with fura-2. Farnesol metabolites, according to particular aspects of the present invention, were observed to be significantly less active than farnesol on neuronal voltage-gated L-type $Ca^{2+}$ channels.

Alcohol withdrawal syndrome can be a life-threatening event for alcoholic patients. The symptoms are for a large part caused by profound changes in the activity of ion channels expressed in the central nervous system. Particular aspects of the present invention demonstrate a novel effect of isoprenoid-based compounds (e.g., farnesol) or dehydroisoprenoid-based compounds, on alcohol withdrawal (AW) seizures, and identify preferred and exemplary isoprenoid-based compounds (e.g., farnesol and analogues thereof) with $Ca^{2+}$ channel blocker properties for use in treating AW seizures and related AW conditions.

Convulsive seizures, can be a life-threatening events for patients. The symptoms are for a large part caused by profound changes in the activity of ion channels expressed in the central nervous system. Particular aspects of the present invention demonstrate a novel effect of isoprenoid-based compounds (e.g., farnesol) or dehydroisoprenoid-based compounds, on convulsive seizures, and identify preferred and exemplary isoprenoid-based compounds (e.g., farnesol and analogues thereof) with $Ca^{2+}$ channel blocker properties for use in treating convulsive seizures and related conditions.

According to preferred aspects, isoprenoid-based compounds (e.g., farnesol and analogues thereof) or dehydroisoprenoid-based compounds, effectively suppress AW1 seizures in the animal, and specific structural modifications of farnesol can change farnesol recognition by farnesol-specific metabolic enzymes while preserving or enhancing activity on $Ca^{2+}$ channels. According to particular aspects of the present invention, calcium channel blockers with a broad spectrum of activity (e.g., active on more than one class of voltage-gated $Ca^{2+}$ channels) are substantial utility for the treatment of alcohol withdrawal syndrome (AWS) and related conditions.

According to preferred aspects, isoprenoid-based compounds (e.g., farnesol and analogues thereof) or dehydroisoprenoid-based compounds, effectively suppress convulsive seizures in the animal, and specific structural modifications of farnesol can change farnesol recognition by farnesol-specific metabolic enzymes while preserving or enhancing activity on $Ca^{2+}$ channels. According to particular aspects of the present invention, calcium channel blockers with a broad spectrum of activity (e.g., active on more than one class of voltage-gated $Ca^{2+}$ channels) are substantial utility for the treatment of convulsive seizure and related conditions.

Preferred embodiments provide pharmaceutical compositions comprising isoprenoid-based compounds (e.g., farnesol and analogues or derivates thereof) or dehydroisoprenoid-based compounds, and methods for using same in treating alcohol withdrawal syndrome (AWS) and alcohol-associated neurological symptoms including, but not limited to depression, tremor, anxiety, autonomic hyperactivity (e.g., sweating, increased blood pressure, tachycardia), hallucinations, seizures, delirium tremens (DT), and memory loss. Alternate preferred embodiments provide pharmaceutical compositions comprising isoprenoid-based compounds (e.g., farnesol and analogues or derivates thereof) or dehydroisoprenoid-based compounds, and methods for using same in treating convulsive seizure and related conditions.

Preferably, the inventive compositions and methods are for treatment (e.g., suppression), including prevention, etc., of alcohol withdrawal seizures in alcohol dependent subjects.

Particular aspects provide a method for the treatment of alcohol withdrawal syndrome, comprising administering to a subject in need thereof a therapeutically effective amount of a compound of formula I:

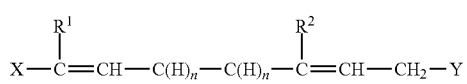

wherein X is:

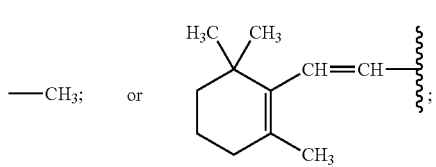

Y is: —OH;

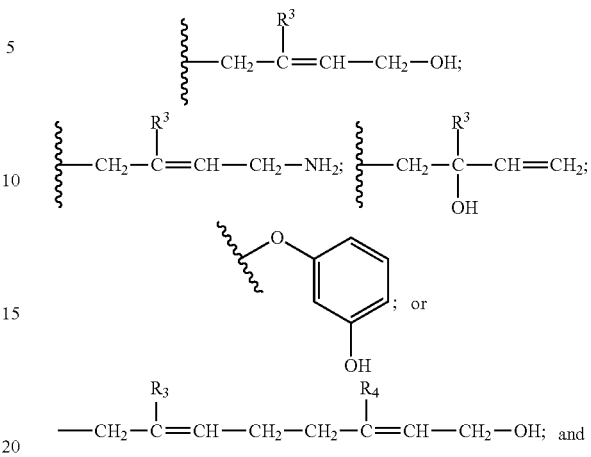

n is 1 or 2; and
$R^1$, $R^2$, $R^3$ and $R^4$ are independently $C_1$-$C_6$ alkyl, $C_1$-$C_6$ alkyl having 0-3 halogen substituents (preferably F), or —$CR^4R^5R^6$ where $R^4$, $R^5$ and $R^6$ are independently selected from H, F, Cl, Br and I (preferably from H, F and Cl, and even more preferably from H and F), or a pharmaceutically acceptable salt of said compound.

Preferably, the compound is of formula II:

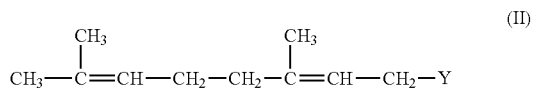

wherein the double bonds are trans (E,E), and wherein Y, $R^3$ and $R^4$ are as described for claim 1, or a pharmaceutically acceptable salt of said compound.

Particular compounds of the present invention comprise asymmetric carbon atoms (e.g., optical or chiral centers) or double bonds, and the racemates, diasteriomers, geometric isomers and individual isomers, enantiamers (e.g., (R) or (S)), etc., are all intended, according to particular aspects of the present invention, to be encompassed within the scope of the present invention. Additionally, in particular embodiments, isotopic variations, whether radioactive (e.g., $^3H$, $^{125}I$, $^{131}I$, $^{14}C$, $^{32}P$, $^{111}In$, $^{90}Y$, etc.) or not, are likewise intended to be encompassed within the scope of the present invention.

Preferably, the compound is at least one selected from the group consisting of: (2E,6E)-3,7,11-trimethyldodeca-2,6, 10-trien-1-ol (all-trans farnesol); (2Z,6E)-3,7,11-trimethyldodeca-2,6,10-trien-1-ol (cis-farnesol); (E)-3,7,11-trimethyldodeca-1,6,10-trien-3-ol (nerolidol); (2E,6E)-3,7,11-trimethyldodeca-2,6,10-trien-1-amine (farnesylamine); (E)-3-(3,7-dimethylocta-2,6-dienyloxy)phenol (geranylresorcinol); (2E,6E)-,7,11-dimethyl-3-(trifluoromethyl)dodeca-2,6,10-trien-1-ol (trifluorofarnesol); (2E,4E, 6E,8E)-3,7-dimethyl-9-(2,6,6-trimethylcyclohex-1-enyl) nona-2,4,6,8-tetraen-1-ol (all-trans retinol); and geraniol; and geranylgerianiol.

Preferably, the treatment of alcohol withdrawal syndrome, comprises treating at least one symptom selected from the group consisting of tremor, anxiety, autonomic hyperactivity, sweating, increased blood pressure, tachycardia, hallucinations, alcohol withdrawal seizures and delirium tremens (DT).

Preferably, the treatment of alcohol withdrawal syndrome, comprises treating alcohol withdrawal seizures. Preferably, the treatment of alcohol withdrawal syndrome, comprises treating delirium tremens (DT). Preferably, the subject is human.

Preferably, administration is via intranasal delivery of at least one of an aerosolized composition, and a nebulized composition. Preferably, administration is via pulmonary delivery. Preferably, pulmonary delivery is via intranasal delivery of at least one of an aerosolized composition, and a nebulized composition.

In particular embodiments, the compound is administered from 1 to 3 times per day.

Additionally, the inventive compositions and methods are used for treatment (e.g., suppression), including prevention, etc., of convulsive seizures in subjects (e.g., humans).

Particular aspects provide a method for the treatment of convulsive seizure, comprising administering to a subject in need thereof a therapeutically effective amount of a compound of formula I:

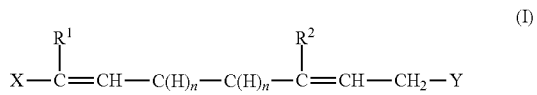

wherein X is:

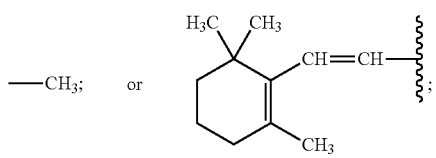

Y is: —OH;

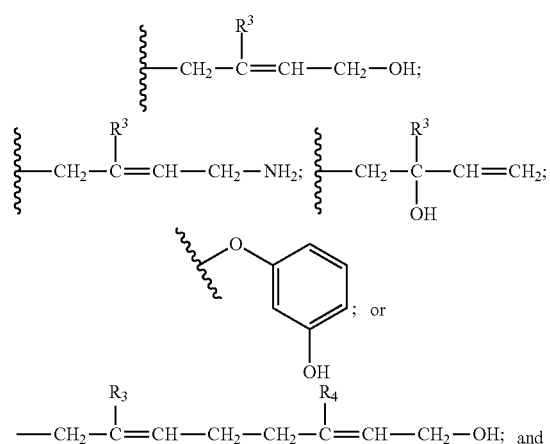

n is 1 or 2; and
$R^1$, $R^2$, $R^3$ and $R^4$ are independently $C_1$-$C_6$ alkyl, $C_1$-$C_6$ alkyl having 0-3 halogen substituents (preferably F), or —$CR^4R^5R^6$ where $R^4$, $R^5$ and $R^6$ are independently selected from H, F, Cl, Br and I (preferably from H, F and Cl, and even more preferably from H and F), or a pharmaceutically acceptable salt of said compound, and wherein the convulsive seizure is non-alcohol related.

Preferably, the compound is of formula II:

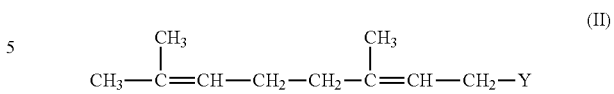

wherein the double bonds are trans (E,E), and wherein Y, $R^3$ and $R^4$ are as described for claim 1, or a pharmaceutically acceptable salt of said compound, and wherein the convulsive seizure is non-alcohol related.

Particular compounds of the present invention comprise asymmetric carbon atoms (e.g., optical or chiral centers) or double bonds, and the racemates, diasteriomers, geometric isomers and individual isomers, enantiamers (e.g., (R) or (S)), etc., are all intended, according to particular aspects of the present invention, to be encompassed within the scope of the present invention. Additionally, in particular embodiments, isotopic variations, whether radioactive (e.g., 3H, $^{125}$I, $^{131}$I, $^{14}$C, $^{32}$P, $^{111}$In, $^{90}$Y, etc.) or not, are likewise intended to be encompassed within the scope of the present invention.

Preferably, the compound is at least one selected from the group consisting of: (2E,6E)-3,7,11-trimethyldodeca-2,6,10-trien-1-ol (all-trans farnesol); (2Z,6E)-3,7,11-trimethyldodeca-2,6,10-trien-1-ol (cis-farnesol); (E)-3,7,11-trimethyldodeca-1,6,10-trien-3-ol (nerolidol); (2E,6E)-3,7,11-trimethyldodeca-2,6,10-trien-1-amine (farnesylamine); (E)-3-(3,7-dimethylocta-2,6-dienyloxy)phenol (geranylresorcinol); (2E,6E)-,7,11-dimethyl-3-(trifluoromethyl)dodeca-2,6,10-trien-1-ol (trifluorofarnesol); (2E,4E,6E,8E)-3,7-dimethyl-9-(2,6,6-trimethylcyclohex-1-enyl) nona-2,4,6,8-tetraen-1-ol (all-trans retinol); and geraniol; and geranylgerianiol.

Preferably, the non-alcoholic convulsive seizure is at least one selected from the group consisting of: partial epileptic seizures; generalized epileptic seizures; absence seizures; myoclonic seizures; clonic seizures; tonic seizures; tonic-clonic seizures; atonic seizures; pseudoepileptic or non-epileptic seizures caused by cardiovascular disease, toxic or metabolic disorders including hypoglycemia and drug toxicity, or sleep disorders; non-epileptic seizures induced by psychiatric conditions including hysteria and schizophrenia; convulsions or seizures caused by acquired immunodeficiency syndrome (AIDS), Parkinson's disease, Alzheimer's disease, other neurodegenerative disease including Huntington's chorea, schizophrenia, obsessive compulsive disorders, tinnitus, neuralgia, trigeminal neuralgia, post-traumatic epilepsy, intoxication or withdrawal from barbiturates, brain illness or injury, brain tumor, choking, drug abuse, electric shock, fever, head injury, heart disease, heat illness, high blood pressure, meningitis, poisoning, stroke, toxemia of pregnancy, uremia related to kidney failure, venomous bites and stings, withdrawal from benzodiazepines, febrile convulsions, and afebrile infantile convulsions. Preferably, the convulsive seizure is a partial or generalized epileptic seizure. Preferably, the subject is human.

Preferably, administration is via intranasal delivery of at least one of an aerosolized composition, and a nebulized composition. Preferably, administration is via pulmonary delivery. Preferably, pulmonary delivery is via intranasal delivery of at least one of an aerosolized composition, and a nebulized composition.

In particular embodiments, the compound is administered from 1 to 3 times per day.

Therefore, various aspects provide one or more genera of isoprenoid-based compounds (e.g., farnesol and analogues thereof) (e.g., "cis' farnesol, nerolidol, geranylresorcinol (GR), farnesylamine, and retinol) that show, relative to farnesol, comparable or enhanced inhibitory activity in vitro on voltage-gated L-type (vascular and neuronal) $Ca^{2+}$ channels. According to preferred aspects, several of these active compounds have structural or functional properties (relative activity reversibility) that reduce their metabolic clearance rate compared to that of farnesol. Such preferred analogues are thus more active on withdrawal seizures in alcohol-dependent subjects, or on convulsive seizures, than farnesol at an equivalent dose.

In particularly preferred aspects, at least one of (2E,6E)-3,7,11-trimethyldodeca-2,6,10-trien-1-amine (farnesylamine), (2E,4E,6E,8E)-3,7-dimethyl-9-(2,6,6-trimethylcyclohex-1-enyl)nona-2,4,6,8-tetraen-1-ol (all-trans retinol; retinol), and (E)-3-(3,7-dimethylocta-2,6-dienyloxy)phenol (geranylresorcinol) are used in pharmaceutical compositions and novel methods for treating convulsive seizures, or for treating alcohol withdrawal syndrome (AWS) and associated neurological symptoms including, but not limited to depression, tremor, anxiety, autonomic hyperactivity (e.g., sweating, increased blood pressure, tachycardia), hallucinations, seizures, delirium tremens (DT), and memory loss.

Most preferably, (2E,6E)-3,7,1-trimethyldodeca-2,6,10-trien-1-amine (farnesylamine) is used. Additional preferred compounds are halogenated compounds (preferably F and Cl, and even more preferably from F) having, according to particular aspects of the present invention, increased serum half-life.

According to additional aspects of the invention, compounds that target and inhibit enzymes that degrade/metabolize/inactivate, for example farnesol and/or farnesol analogues or derivatives are used to induce endogenous accumulation of farnesol and suppress/prevent seizures.

In particular aspects, the inventive methods comprise administering to a subject in need thereof a therapeutically effective amount of a isoprenoid-based compound (e.g., farnesol compound), wherein the convulsive seizure is non-alcohol related.

Preferably, the convulsive seizure is selected from the group consisting of: partial epileptic seizures; generalized epileptic seizures; absence seizures; myoclonic seizures; clonic seizures; tonic seizures; tonic-clonic seizures; atonic seizures; pseudoepileptic or non-epileptic seizures caused by cardiovascular disease, toxic or metabolic disorders including hypoglycemia and drug toxicity, or sleep disorders; non-epileptic seizures induced by psychiatric conditions including hysteria and schizophrenia; convulsions or seizures caused by acquired immunodeficiency syndrome (AIDS), Parkinson's disease, Alzheimer's disease, other neurodegenerative disease including Huntington's chorea, schizophrenia, obsessive compulsive disorders, tinnitus, neuralgia, trigeminal neuralgia, post-traumatic epilepsy, intoxication or withdrawal from barbiturates, brain illness or injury, brain tumor, choking, drug abuse, electric shock, fever, head injury, heart disease, heat illness, high blood pressure, meningitis, poisoning, stroke, toxemia of pregnancy, uremia related to kidney failure, venomous bites and stings, withdrawal from benzodiazepines, febrile convulsions, and afebrile infantile convulsions.

Preferably, the convulsive seizure is a partial or generalized epileptic seizure.

Preferably, the subject for the herein described methods is human. Preferably, the isoprenoid-based compound (e.g., farnesol compound) is administered from 1 to 3 times per day. Preferably, administration is via pulmonary delivery. Preferably, pulmonary delivery is via intranasal delivery of at least one of an aerosolized composition, and a nebulized composition.

TABLE 2 provides summary of exemplary representative isoprenoid-based compound (e.g., farnesol and farnesol analogue) data from the inventive EXAMPLES provided herein below.

TABLE 2

Structural and functional properties of isoprenoid-based compounds (e.g., farnesol and farnesol analogues) with anti-seizure activity according to aspects of the present invention.

| Compound | CLogP (reversibility) | Activity on voltage-gated $Ca^{2+}$ channels | | | Metabolism | | Predicted anti-seizure activity |
| | | L-type (cardiac) | L-type (neuronal) | N-type | ADH | FolDH | |
| --- | --- | --- | --- | --- | --- | --- | --- |
| All-trans farnesol | 5.0 (+) | ++ | ++ | ++ | ++ | ++ | ++ |
| "Cis" farnesol | 5.0 (+) | +++ | +++ | nd | + | + | +++ |
| Nerolidol | 4.78 (nd) | nd | +++ | nd | +/− | − | +++ (la) |
| Retinol | 6.40 (−) | ++ | ++ | ++ | ++ | nd | ++ (la) |
| Geranylresorcinol | 5.31 (−) | ++ | +++ | nd | − | − | +++ (la) |
| Farnesylamine | 5.10 (−) | +++ | +++ | nd | − | − | ++++ (la) |
| Trifluorofarnesol* | 4.82 (nd) | nd | nd | nd | (−) | (−) | (+++) (la) |

Metabolism by intracellular dehydrogenases should be reduced as compared to farnesol. Antiseizure activity is based on the assumption that trifluorofarnesol will be as active as farnesol on $Ca^{2+}$ channels.
(nd = not determined; la = long-acting). Predicted antiseizure activity (+) is based on effect on L-type $Ca^{2+}$ channels, CLogP and reversibility or ADH-FolDH recognition when available. The ++ farnesol activity was arbitrary.

Definitions

The terms 'treating' and 'treatment' refer to any treatment of a disease in a mammal, particularly a human, and generally include: (i) preventing the disease from occurring in a subject which may be predisposed to the disease but has not yet been diagnosed as having it; (ii) inhibiting the disease, i.e., arresting its development; or (iii) relieving the disease, i.e., causing regression of the disease. Treating also refers to providing a beneficial alteration in one or more of the symptoms of a disease state or reducing or eliminating the disease state itself. It will be appreciated that a beneficial alteration can include transitory or permanent reduction or elimination of the symptom. It will also be appreciated that 'treating' can also involve a reduction in actual adverse consequences or a reduction in the likelihood of adverse consequences of a pathological state. Thus treatment as used herein can also refer to prophylaxis. For example, treatment of AW seizure can involve actual reduction or prevention thereof.

The term 'effective amount' is intended to mean the amount of a drug, or multidrug therapeutic, which achieves a positive outcome on one or more symptoms of a disease state or which acts prophylactically to reduce the likelihood of one or more pathological symptoms or consequences of a disease state. Thus, for example, an effective amount of a drug for the treatment of AWS can refer to an amount of a drug sufficient to transiently or permanently reduce AW seizures or to reduce the likelihood of the onset of AW seizures.

The term "administering" when used in the context of, for example, "administering to a mammal" refers to delivering the drugs in question to a subject organism (e.g., mammal). Administration can be topical, intraperitoneal, subdermal, i.v., via inhalation, etc., as described herein.

The term "pharmacologically acceptable excipient" or "pharmaceutically acceptable excipient" refers to a diluent or excipient suitable for administration to an organism. Administration can be, for example, topical or systemic, directed to particular tissues, organs or cells. The excipient is-essentially a carrier agent to facilitate administration of the active ingredient (e.g., farnesol and or analogues or derivatives thereof). The excipient may contain auxiliary substances as required to approximate physiological conditions, such as pH adjusting and buffering agents, tonicity adjusting agents, wetting agents, solubilizers, emulsifiers and the like.

The term "contacting a cell" when referring to contacting with a drug is used herein to refer to contacting in a manner such that the drug is internalized into the cell or into specific cellular components (e.g., plasma membrane). Where the drug is lipophilic or complexed with a lipid (e.g., a cationic lipid) simple contacting will result in transport (active and/or diffusive) into the cell. Alternatively the drug may itself be actively transported into the cell or may be administered with a carrier composition that is actively transported into the cell.

The term "pharmaceutically acceptable salts" refers to salts of the subject compounds which possess the desired pharmacological activity and which are neither biologically nor otherwise undesirable.

The term "isoprenoid-based compound" and/or "farnesol compound" refers to a compound genus as discussed herein (formulas I and II) minimally encompassing (2E,6E)-3,7, 11-trimethyldodeca-2,6,10-trien-1-ol (all-trans farnesol); (2Z,6E)-3,7,11-trimethyldodeca-2,6,10-trien-1-ol (cis-farnesol); (E)-3,7,11-trimethyldodeca-1,6,10-trien-3-ol (nerolidol); (2E,6E)-3,7,11-trimethyldodeca-2,6,10-trien-1-amine (farnesylamine); (E)-3-(3,7-dimethylocta-2,6-dienyloxy)phenol (geranylresorcinol); (2E,6E)-,7,11-dimethyl-3-(trifluoromethyl)dodeca-2,6,10-trien-1-ol (trifluorofarnesol); (2E,4E,6E,8E)-3,7-dimethyl-9-(2,6,6-trimethylcyclohex-1-enyl)nona-2,4,6,8-tetraen-1-ol (all-trans retinol), and related analogues and derivatives thereof. Particular compounds of the present invention comprise asymmetric carbon atoms (e.g., optical or chiral centers) or double bonds, and the racemates, diasteriomers, geometric isomers and individual isomers, enantiamers (e.g., (R) or (S)), etc., are all intended, according to particular aspects of the present invention, to be encompassed within the scope of the present invention. Additionally, in particular embodiments, isotopic variations, whether radioactive (e.g., $^3$H, $^{125}$I, $^{131}$I, $^{14}$C, $^{32}$P, $^{111}$In, $^{90}$Y, etc.) or not, are likewise intended to be encompassed within the scope of the present invention. The isoprenoid-based and dehydroisoprenoide-based compounds of the present invention can be in the form of pharmaceutically acceptable salts, esters or amides (e.g., esters or amides of palmitoic acid).

The term "convulsive seizure", according to the present invention, generally refers to non-alcoholic convulsions comprising involuntary muscle contractions caused by abnormal neuronal activity resulting in contortion of the body and/or limbs. Seizures according to this invention are transient changes of behavior induced by the disordered, synchronous and rhythmic firing of neurons. For purposes of the present invention, alcohol withdrawal seizures are discussed and considered separately from non-alcoholic convulsive seizures as used herein.

A. Use of Isoprenoid-Based Compounds (e.g., Farnesol and/or Farnesol Analogues) to Treat Alcohol Withdrawal Syndrome (AWS) or to Treat Convulsive Seizure.

Farnesol; Pharmacological Properties.

Farnesol-[(2Z,6Z)-3,7,11-trimethyldodeca-2,6,10-trien-1-ol], is an isoprene-based, 15-carbon primary alcohol that occurs naturally in plants, yeast and mammals, and is known to have psychotropic activity in rodents and fish (Binet, 1972a-c, 1975a,b; showing that farnesol induces sedation in the mouse and the fish, decreases caffeine-induced excitation (mouse), and decreases aggressiveness (in fish)).

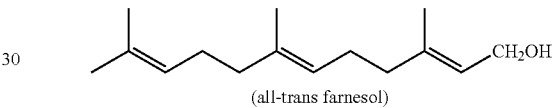

(all-trans farnesol)

Farnesol is known to not prevent pentylenetetrazole-induced seizures and has no intrinsic hypnotic or cataleptigenic activity. However, it enhances the hypnotic activity of barbiturates and potentiates both the cataleptigenic and anti-psychotic activities of haloperidol. Farnesol is a psycho-sedative substance, which is most efficient in excitatory states and is capable of reinforcing the activity of hypnotic and neuroleptic agents.

Preferred embodiments provide pharmaceutical compositions comprising isoprenoid-based compounds (e.g., farnesol and/or farnesol analogues or derivatives), and methods for using same in treating alcohol withdrawal syndrome (AWS) and associated neurological symptoms including, but not limited to depression, tremor, anxiety, autonomic hyperactivity (e.g., sweating, increased blood pressure, tachycardia), hallucinations, AW seizures, delirium tremens (DT), and memory loss. Alternate embodiments provide pharmaceutical compositions comprising isoprenoid-based compounds (e.g., farnesol and/or farnesol analogues or derivatives), and methods for using same in treating convulsive seizure.

Treatment of AWS and AW seizure, or treatment of convulsive seizure, using isoprenoid-based compounds (e.g., farnesol and/or farnesol analogues or derivatives) typically involves: first diagnosing the condition (e.g., alcohol related condition (e.g., AWS)) and determining whether treatment is appropriate; administration of a isoprenoid-based compound (e.g., farnesol and/or farnesol analogues or derivatives) alone or in combination with one or more other drug(s) in a therapeutic regimen, monitoring response of the subject, and, if necessary, altering/optimizing dosage/treatment regimen. Methods of diagnosing AWS and AW seizure, or convulsive seizure, are well known to those of skill in the art.

Cellular and Molecular Mechanism of Action of Farnesol—

Without being bound by mechanism, farnesol is a potent inhibitor of $Ca^{2+}$-dependent arterial smooth muscle contractions and lowers blood pressure in the animal (Roullet, 1996; Luft, 1999). Farnesol's effect on arteries is reversible and dose-dependent ($IC_{50}$~2.0 µM), and is mediated by inhibition of voltage-gated L-type $Ca^{2+}$ channels, the ion channels that regulate calcium entry in vascular smooth muscle cells (Roullet, 1997, Luft, 1999). Farnesol, at micromolar concentration, inhibits both the cardiac and neuronal L-type $Ca^{2+}$ channels, as well as the N-type $Ca^{2+}$ channels, but is inactive on the R- or P/Q-type $Ca^{2+}$ channels (Roullet, 1999; using PC12 cells that express the neuronal subtype—$\alpha_{1D}$— of L-type $Ca^{2+}$ channels, and using HEK cells expressing either one of the four major types of pore-forming subunits of the high voltage-activated calcium channels: $\alpha_{1A}$ (P/Q-type), $\alpha_{1B}$ (N-type), $\alpha_{1C}$ (cardiac, L-type), $\alpha_{1E}$ (R-type)). Farnesol, at sub-micromolar concentrations, has a selective affinity for the N-type $Ca^{2+}$ channel in its inactivated state, leading to significant block (~50% at 250 nM farnesol) of the channel at typical neuronal resting membrane potential.

B. Formulations and Delivery Methods.

For use as treatment of animal subjects, the compounds of the invention can be formulated as pharmaceutical or veterinary compositions. Depending on the subject to be treated, the mode of administration, and the type of treatment desired, e.g., prevention, prophylaxis, therapy; the compounds are formulated to conform with these parameters. A summary of such techniques is found in Remington's Pharmaceutical Sciences, latest edition, Mack Publishing Co., Easton, Pa. Generally, for use in treatment, the compounds of the invention may be used alone, as mixtures of two or more compounds of the invention or in combination with other pharmaceuticals. Depending on the mode of administration, the compounds will be formulated into suitable compositions to permit facile delivery.

The isoprenoid-based and dehydroisoprenoide-based compounds of the present invention can be in the form of pharmaceutically acceptable salts, esters or amides (e.g., esters or amides of palmitoic acid). Prodrug forms of the isoprenoid-based and dehydroisoprenoide-based compounds all also encompassed within the scope of the present invention.

Formulations may be prepared in a manner suitable for systemic administration or topical or local administration. Systemic formulations include, for example, those designed for injection (e.g., intramuscular, intravenous or subcutaneous injection), or may be prepared for transdermal, transmucosal, or oral administration. The formulation will generally include a diluent as well as, in some cases, adjuvants, buffers, preservatives and the like. The compounds can be administered also in liposomal compositions or as microemulsions. Thus, once formulated, the compositions of the invention can be administered directly to the subject. Direct delivery of the compositions will generally be accomplished by parenteral injection, e.g., subcutaneously, intraperitoneally, intravenously or intramuscularly, or to the interstitial space of a tissue. Other modes of administration include oral and pulmonary (e.g., inhalation) administration, suppositories, and transdermal applications, needles. Dosage treatment can be a single dose schedule or a multiple dose schedule. Preferably, from 1 to about 3 doses are administered per day. Preferably, doses are administered once or twice before, for example, alcohol withdrawal during detox sessions, and preferably once at the onset of seizure.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised (see, e.g., U.S. Pat. No. 5,624,677, incorporated by reference herein). Systemic administration may also include relatively noninvasive methods such as the use of suppositories, transdermal patches, transmucosal delivery and intranasal administration (e.g., via the paranasal sinus membranes). Oral administration is also suitable for compounds of the invention. Suitable forms include syrups, capsules, tablets, and the like, all as in understood in the art.

In preferred embodiments, the inventive farnesol compounds are administered to the subject's lungs by inhalation; for example by intranasal delivery of an aerosolized or nebulized pharmaceutical composition.

For administration to animal or human subjects, the dosage of the compounds of the invention is preferably in the range of about 0.1 to about 200 µg/kg, from about 0.2 to about 1 mg/Kg, from about 1 to about 400 mg/Kg, from about 25 to about 200 mg/Kg, or from about 50 to about 200 mg/kg. Most preferably, the range is from 1 to about 400 mg/Kg, from about 25 to about 200 mg/Kg, or from about 50 to about 200 mg/kg. Even more preferably, the range is from about 25 to about 200 mg/Kg, or from about 50 to about 200 mg/kg. However, dosage levels are highly dependent on the nature of the condition, the condition of the patient, the judgment of the practitioner, and the frequency and mode of administration, and one of skill in the art will be able to adjust the dosage to conform to the conditional attributes.

Additional guidance on formulation and delivery of farnesol compounds according to the present invention is provided by U.S. Pat. No. 6,437,003 to Roullet et al. (disclosing methods for treating stroke with retinoids), and U.S. Pat. No. 6,267,945 to Zamponi et al., both of which are incorporated by reference herein in their entirety.

Example 1

The Activity of Farnesol Metabolites on Neuronal Voltage-Gated L-Type $Ca^{2+}$ Channels was Investigated Structural Selectivity of the $Ca^{2+}$ Channel Blocker Activity of Farnesol—

The 15-carbon isoprenoid structure of farnesol has activity on $Ca^{2+}$ channels, whereas the shorter (C10, geraniol) and longer (C20, geranylgeraniol) isoprenols are inactive (Roullet, 1996, 1997).

Farnesol is transformed into farnesal and farnesoic acid by intracellular dehydrogenases: cytosolic ADH and AlDH (Christophe, 1961; Waller, 1965; Keung, 1991), microsomal farnesol and farnesal dehydrogenases (FolDH; FalDH; P450 enzymes) and mitochondrial/peroxisomal dehydrogenases (Westfall, 1997; Bentinger, 1997; DeBarber, 2004). Alternatively, farnesol is transformed into farnesyl-PP by specific intracellular kinases (Westfall, 1997; Bentinger, 1997).

According to particular aspects of the present invention, the alcohol group is essential for activity. Additionally, the activity of farnesol metabolites on neuronal voltage-gated L-type $Ca^{2+}$ channels was investigated. FIG. 1 shows that farnesol metabolites are significantly less active than farnesol on neuronal voltage-gated L-type $Ca^{2+}$ channels. The $Ca^{2+}$ channel activity is expressed as % inhibition of KCl-induced intracellular $Ca^{2+}$ signaling in non-NGF differentiated PC12 cells loaded with fura-2 (see Materials and Methods under Example 2). The assayed molecules are: FPP—farnesyl pyrophosphate; FOH—all-trans farnesol; FCHO—all-trans farnesal; and FCOOH—all-trans farnesoic acid (prepared by Dr. McDougal). All analogues were observed to be significantly less activity than FOH (mean±SE; n=5-6/group), and farnesyl-PP and farnesoic acid were substantially inactive.

The data indicate that both metabolism and structural modifications that increase the electronegativity of farnesol will reduce farnesol activity on ion channels.

Example 2

Farnesol was Shown to be Effective in Suppressing Alcohol Withdrawal Seizures in Two Mice Strains that are Art-Recognized and Widely Accepted Models of Alcoholism and Alcohol Withdrawal Syndrome Experiments were conducted to examine whether farnesol would suppress alcohol withdrawal seizures in alcohol-dependent mouse strains. According to preferred aspects of the present invention, farnesol effectively suppressed alcohol withdrawal seizures in animals.

Materials and Methods

Mouse Strains— experiments were conducted in two mouse strains: Withdrawal Seizure Prone replicate 1 (WSP1); and DBA/2J. WSP1 mice have been selectively bred for their high sensitivity to ethanol and enhanced expression of alcohol withdrawal seizures (Kosobud, 1995; Metten, 1996). DBA/J2 mice also have pronounced alcohol withdrawal symptoms following either chronic treatment or a single injection of a hypnotic dose of alcohol (Crabbe, 1983; Metten, 1994; Crabbe & Metten, in preparation), but are sometimes preferred to the WSP1 mice for the screening of anti-AWS drugs, because of their lower basal level of convulsions (in the absence of alcohol).

WSP1 Male Mice— the animals (77-107 days old WSP1 male mice; 28.4±0.5 g body weight; n=16-17 group) were tested for baseline HIC severity twice, 20-30 minutes apart. The animals were then weighed, injected with 4 g/kg ethanol, and assessed for acute withdrawal at hourly intervals from 2-10 hours after injection. Immediately after the hour-7 time point HIC score (a time of maximal withdrawal in this strain), animals were injected with either 200 mg/kg farnesol (suspension in saline containing 3 g/l bovine serum albumin) or vehicle, and scored 8, 16, 24, 32, 40, 48 and 56 minutes later using a scale from 0 to 7 (Crabbe, 1991; scoring scale shown in TABLE 1).

TABLE 1

| HIC rating scale (adapted from Crabbe, 1991) | |
|---|---|
| Symptom | Score |
| Spontaneous, severe, tonic-clonic convulsion (quick onset, long duration) | 7 |
| Severe, tonic-clonic convulsion when lifted by the tail (quick onset, long duration) | 6 |

TABLE 1-continued

| HIC rating scale (adapted from Crabbe, 1991) | |
|---|---|
| Symptom | Score |
| Tonic-clonic convulsion when lifted by the tail (delayed onset) | 5 |
| Tonic convulsion when lifted by the tail | 4 |
| Tonic-clonic convulsion after gentle 180° spin | 3 |
| No convulsion when lifted by the tail but tonic convulsion elicited by gentle 180° spin | 2 |
| Only facial grimace after gentle 180° spin | 1 |
| No convulsion | 0 |

The time course was then resumed (animals were scored at hour 8, etc.). The dose of farnesol was determined using Binet et al.'s data on farnesol $LD_{50}$ in the mouse and a series of preliminary experiments that showed that a dose of farnesol of 200 mg/kg tended to reduce basal HICs in naïve WSP1 mice.

Dba/2J Mice—

DBA/2J mice (males and females; mean BW=23 g; n=44) were injected intra peritoneally (i.p.) with a loading dose of 1.5 g/kg ethanol (20% v/v saline solution) and with 68.1 mg/kg pyrazole hydrochloride, and then placed for 72 h into inhalation chambers (3-4 animals/cage) set at 5 mg ethanol/L air (Guppy, 1995; Crabbe, 1998). The animals were removed from the chambers after 24 and 48 h, and re-injected with pyrazole. The pyrazole injections are necessary to reduce mortality and heterogeneity in withdrawal reactions (Goldstein, 1972). A second group of animals matched for BW and sex (n=32), were housed under normal ('air-breathing') conditions and served as pyrazole-injected controls. All animals had free access to food and water and were housed with a 12 hr day-night light cycle. Upon withdrawal from the chambers (t=0), body weight was determined and a tail blood sample was collected for the determination of blood alcohol concentration (BEC, alcohol-treated animals only; Crabbe, 1998). The animals were then placed in clean home cages, transported to another room and randomly assigned (half of the animals in each group) to receive either farnesol (300 mg/kg, i.p., suspended in saline containing 3 g/l bovine serum) or vehicle (5 µl/g BW). Injections were made either 3 hours (GROUP A) or 6 hours (GROUP B) after withdrawal (approximately half of the animals were used in each group). These time points were chosen to precede peak withdrawal (GROUP A at 3 hours) as it begins to ascend above control levels to determine whether farnesol would prevent withdrawal, and to treat withdrawal at its peak (GROUP B at 6 hours). HICs were scored hourly until injections (0 to 3 h for GROUP A and 0 to 6 h for GROUP B). Immediately after HIC scoring at the hour-3 or hour-6 time points, the animals were injected with farnesol or vehicle, and scored 10, 20, 30 and 40 minutes later. The hourly scoring was then resumed at either 4 hours or 7 hours, and continued to the 10-hour time point.

Results

WSP1 Mice.

The maximum effect of farnesol was observed at the (7 hr) 32 minute time point (not shown), so the peak farnesol effect was measured as the average of the 24, 32, and 40 minute scores versus the vehicle group at the same times. Baseline HICs were 1.75±0.13 and 1.94±0.21 in the vehicle and farnesol groups, respectively (p=NS). The peak withdrawal effect in the vehicle group was 3.42±0.21 vs. 2.67±0.29 in the farnesol group (p<0.05).

Therefore, there was about a 56% reduction in peak ethanol withdrawal by farnesol.

DBA/2J Mice.

Figures 2A, 2B:
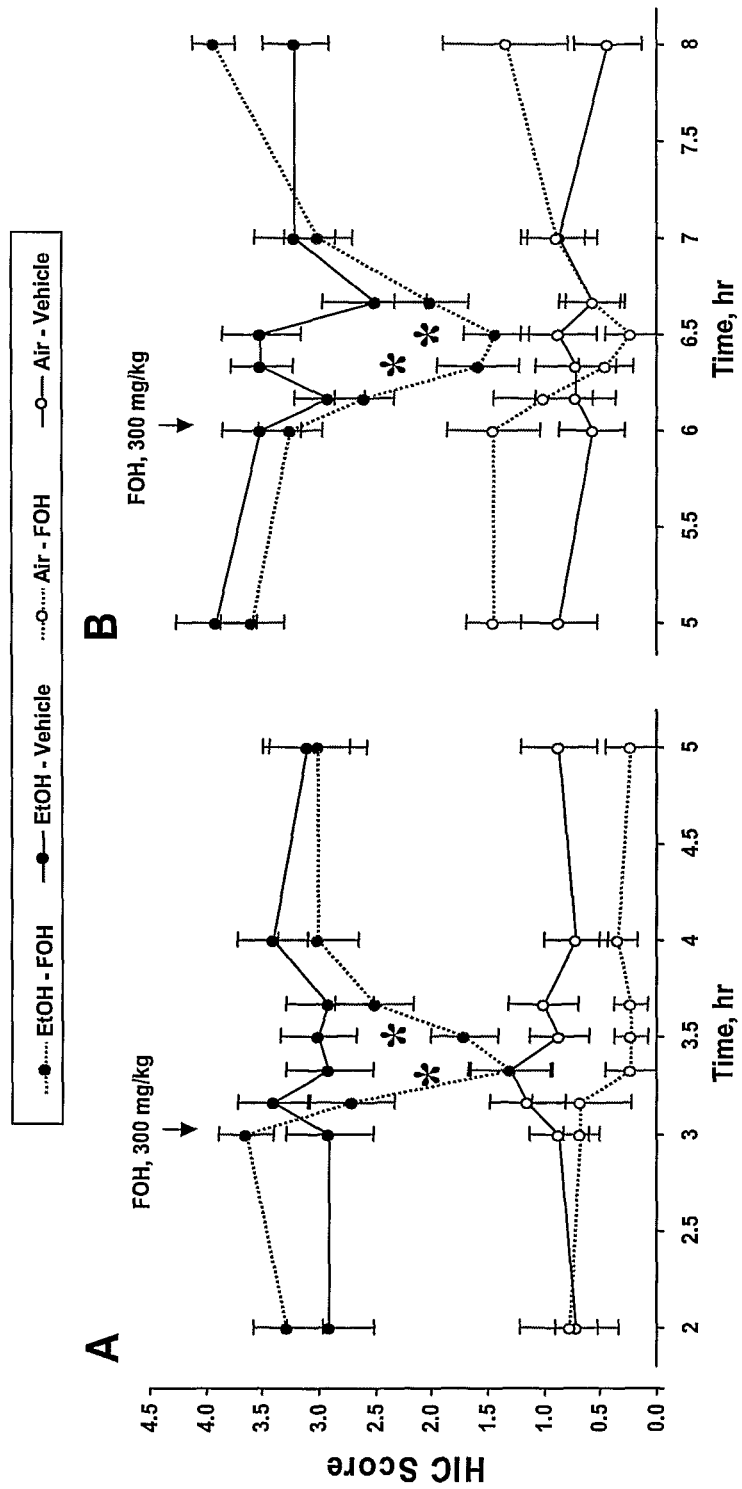
FIGS. 2A and 2B show an analysis of the effect of farnesol administration to ethanol-treated DBA/2J mice. All animals exposed to ethanol had severe withdrawal seizures (average scores ranging from 3 and 4) by the time they were injected at 3 (FIG. 2A) or 6 (FIG. 2B) hours after withdrawal from alcohol. Dotted lines show farnesol-treated animals, whereas solid lines show vehicle-treated animals. Open symbols correspond to 'air-breathing' animals, whereas closed symbols correspond to ethanol-treated animals. The data show, for both GROUPS A and B, that all-trans farnesol suppressed seizures in ethanol-treated DBA/2J mice.

FIGS. 2A and 2B show, for both GROUPS A and B, that all-trans farnesol suppressed seizures in alcoholic DBA/2J mice. All animals exposed to ethanol had severe withdrawal seizures (average scores ranging from 3 and 4) by the time they were injected. Dotted lines show farnesol-treated animals, whereas solid lines show vehicle-treated animals. Open symbols correspond to 'air-breathing' animals, whereas closed symbols correspond to ethanol-treated animals. FIG. 2A shows the group of mice injected 3 hours after withdrawal, whereas FIG. 2B shows the group of mice injected 6 hours after withdrawal. The effect of farnesol was statistically significant (ANOVA) in both GROUPS (A and B) of alcohol-dependent animals. Asterisks ("**") indicate a significant difference ($p<0.05$) with matching vehicle-treated, alcohol-dependent animals. There was no significant effect of farnesol in 'air-breathing' animals. Statistical analysis of the data using ANOVA for repeated measures showed that farnesol injection significantly reduced alcohol withdrawal seizure scores in both GROUP A and GROUP B, and that the effect was time dependent p values for [time*drug] interactions were <0.005 and <0.001 for groups A and B, respectively). The effect of farnesol was reached between 20 and 30 minutes after injection. Percent seizure reduction was 99% and 78% for GROUPS A and B, respectively, and was estimated as the ratio of: the difference between average peak farnesol score and corresponding average vehicle score; with the difference between average vehicle score for air- and ethanol-breathing animals at the time of peak farnesol effect. Seizures returned to pre-injection level in approximately one hour. The farnesol effect, therefore, was pronounced but transient. No death was observed up to 25 hours after farnesol injections. By comparison, average baseline seizure scores in 'air-breathing' control animals were in the range of 0.5 to 1.5. Farnesol injection induced some reduction in HIC scores for the 'air-breathing' control groups, but the effect was not statistically significant ($p=0.39$ and p 0.14 for GROUPS A and B, respectively).

In summary, according to particular aspects of the present invention, farnesol inhibited alcohol withdrawal seizures in two strains of mice (WSP1 and DBA/2J) widely accepted as models in the study of alcoholism and withdrawal syndrome (Metten & Crabbe, 1996). In contrast, it had little or no effect on spontaneous seizures.

Therefore, according to preferred aspects of the present invention, farnesol (e.g., farnesol and/or farnesol analogues or derivatives) has substantial utility in pharmaceutical compositions and methods for treating AWS and associated neurological symptoms including, but not limited to depression, tremor, anxiety, autonomic hyperactivity (e.g., sweating, increased blood pressure, tachycardia), hallucinations, seizures, delirium tremens (DT), and memory loss. The dose necessary to induce complete seizure suppression in the above-described studies was relatively high, but was nonetheless non toxic. Furthermore, the duration of the farnesol effect is relatively short (approximately 1 hour), but reasonably likely to help overcome the worst seizures in alcoholics, at the time they are seen at an emergency room. According to additional preferred embodiments, a sufficiently long action and/or administration is used to protect patients until they are safely out of the seizure window.

Example 3

Screening Methods—Vascular Reactivity and Calcium Signaling; Farnesol Analogues with $Ca^{2+}$ Channel Blocker Properties were Identified Without being bound by mechanism, the above-described (EXAMPLE 2) transient nature of the farnesol effect on alcohol withdrawal seizures is likely explained by active transformation of the injected farnesol into metabolites that are less active (farnesal), or relatively inactive (farnesoic acid and farnesyl-PP; see FIG. 1). Therefore, according to preferred aspects, structural modifications of farnesol analogues are identified and are useful to preclude or slow metabolism by farnesol-specific enzymes. Particularly preferred are those structural modifications/analogues that do not significantly or substantially compromise activity on $Ca^{2+}$ channels, and thus provide effective compounds with prolonged activity in treating alcohol withdrawal seizures.

Materials and Methods

To identify compounds with enhanced L-type $Ca^{2+}$ channel blocker activity, several compounds were either purchased or synthesized, and then tested for their ability to inhibit: (1) KCl-induced contraction in isolated arteries; (2) KCl-induced $Ca^{2+}$ signaling in fura-2 loaded arteries; and (3) KCl-induced $Ca^{2+}$ signaling in fura-2 loaded PC12 cells, all using art-recognized methods established in the applicants' laboratories (Roullet, 1993, 1994, 1995, 1997; De Lima, 1999). Arteries express smooth muscle voltage-gated, L-type ($Ca_v1.2$ or $\alpha_{1C}$ subunit) $Ca^{2+}$ channels, whereas PC12 cells constitutively express the neuronal voltage-gated, L-type ($Ca_v1.3$) $\alpha_{1D}$ subunit (Ertel, 2000).

Results

Commercially Available Analogues.

Various commercially available farnesol analogues were tested.

Figure 3:
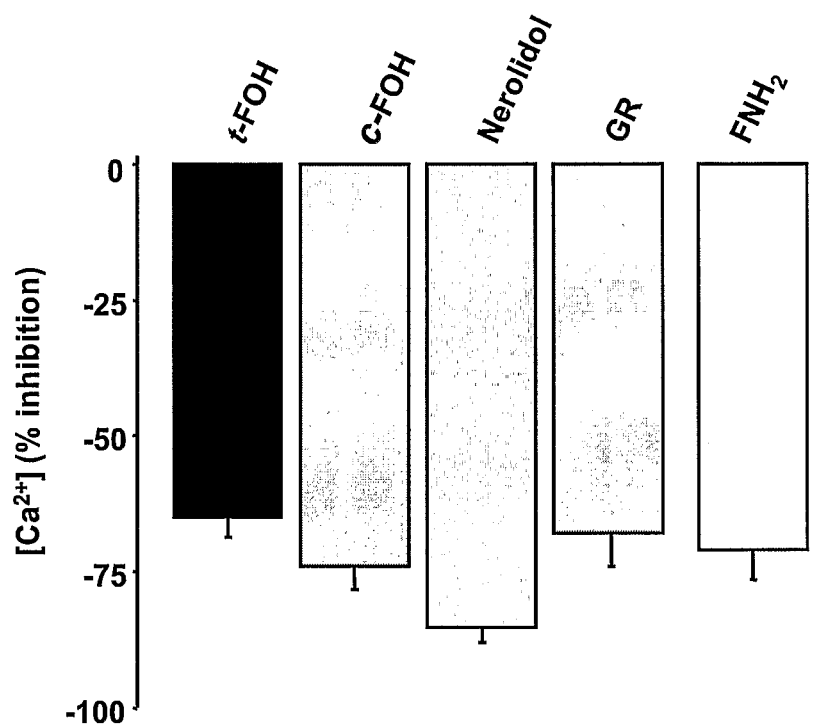
FIG. 3 shows, according to preferred aspects of the present invention, the inhibitory effect of all-trans farnesol, nerolidol, geranylresorcinol, farnesylamine and "cis" farnesol on neuronal voltage-gated L-type $Ca^{2+}$ channel activity. $Ca^{2+}$ channel activity is expressed as % inhibition of KCl-induced intracellular $Ca^{2+}$ signaling in non-NGF treated PC12 cells loaded with fura-2.

FIG. 3 shows, according to preferred aspects of the present invention, the inhibitory effect of all-trans farnesol, nerolidol, geranylresorcinol, farnesylamine and "cis" farnesol on neuronal voltage-gated L-type $Ca^{2+}$ channel activity. $Ca^{2+}$ channel activity is expressed as % inhibition of KCl-induced intracellular $Ca^{2+}$ signaling in non-NGF treated PC12 cells loaded with fura-2. Farnesyl bromide, farnesyl acetate, farnesylacetone and farnesyl methyl ether did not showed significant activity on arteries and were therefore not selected for in vivo testing.

Nerolidol

[(E)-3,7,11-trimethyl-1,6,10-dodecatrien-3-ol]. Nerolidol was tested (FIG. 3, center bar graph) using PC12 cells in culture, and was as effective as, or slightly more effective than all-trans farnesol in blocking KCl-induced $Ca^{2+}$ signaling (~85% block vs. 65% for nerolidol and farnesol respectively; n=3/group). Additionally, according to applicants' studies, and to particular aspects of the present invention, nerolidol is not a substrate for ADH and is not recognized by microsomal FolDH. Therefore, according to preferred inventive aspects, nerolidol is active in vitro on neuronal, L-type $Ca^{2+}$ channels and is more slowly metabolized than all-trans farnesol in vivo.

All-Trans Retinol (Retinol).

All-trans retinol (retinol), like farnesol, is an isoprenoid compound. It is metabolized by class IV ADH and is more hydrophobic than farnesol (C Log P=6.4 vs. 5.0 for retinol and farnesol, respectively). Applicants' prior studies have shown that retinol blocks efficiently smooth muscle and neuronal (PC12 cells) voltage-gated L-type $Ca^{2+}$ channels (see U.S. Pat. No. 6,437,003, entitled "Use of retinoids to treat high blood pressure and other cardiovascular disease," and incorporated by reference herein in its entirety).

Figures 4A, 4B:
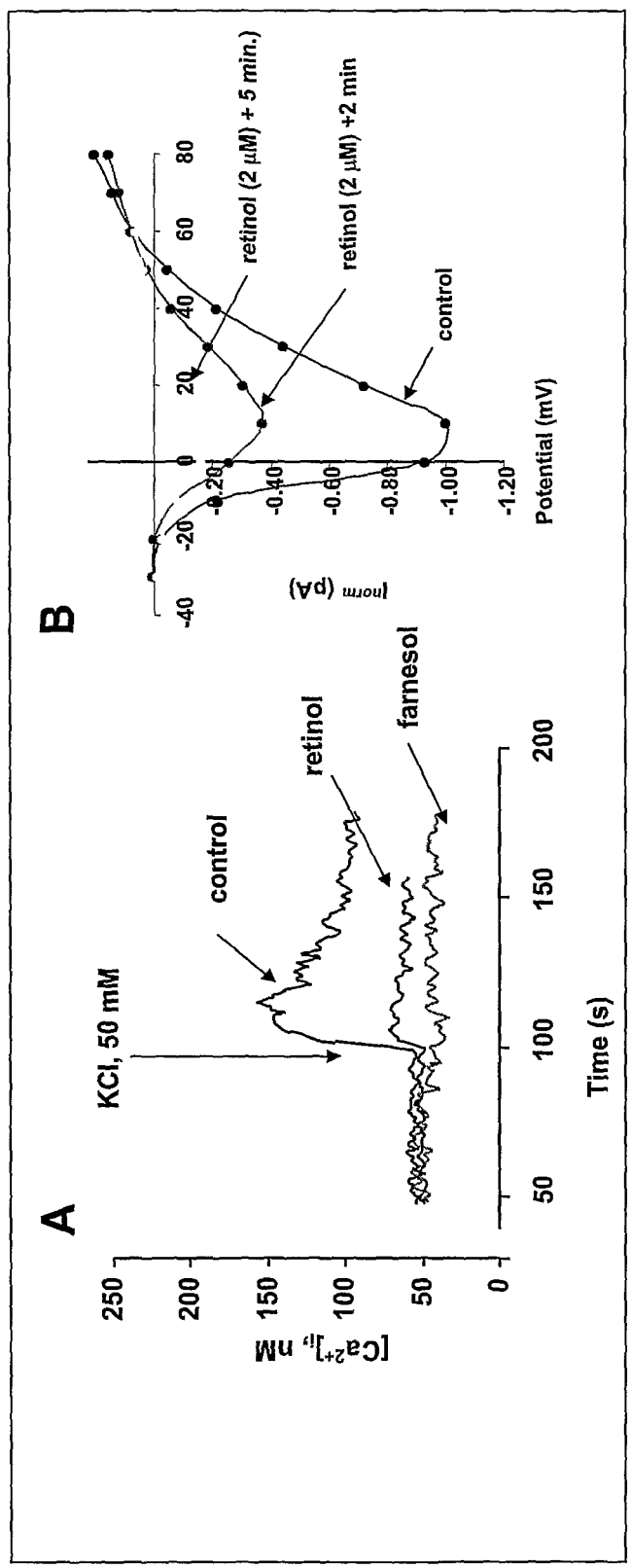
FIGS. 4A and 4B show neuronal ($\alpha_{1D}$ subunit) L-type $Ca^{2+}$ channel ($Ca^{2+}$ signaling in fura-2 loaded PC12 cells) (FIG. 4A); on neuronal ($\alpha_{1B}$ subunit) N-type $Ca^{2+}$ channel ($\alpha_{1B}$-transfected HEK cells; as in Roullet, 1999) (FIG. 4B). Current-voltage relationship (IV) recording conditions were: holding potential (hp)=–100 mV; 20 mM $Ba^{2+}$. Inhibition of N-type currents was ~90% at 5 min. Overall, retinol was shown to be almost as effective as farnesol.

Experiments (FIG. 4) using patch-clamp techniques and HEK cells transfected with human $\alpha_{1B}$ ($Ca_v2.2$) subunits further indicate that, like farnesol, retinol also blocks N-type calcium channels. FIGS. 4A and 4B show, according to preferred aspects of the present invention, the effect of all-trans retinol on: neuronal ($\alpha_{1D}$ subunit) L-type $Ca^{2+}$ channel (Ca$^{2+}$ signaling in fura-2 loaded PC12 cells) (FIG. 4A); an on neuronal ($\alpha_{1B}$ subunit) N-type Ca$^{2+}$ channel ($\alpha_{1B}$-transfected HEK cells; as in Roullet, 1999) (FIG. 4B). IV recording conditions were: Hp=−100 mV; 20 mM Ba$^{2+}$. Inhibition of N-type currents was ~90% at 5 min.

Overall, therefore, retinol is almost as potent as farnesol (IC$_{50}$ on L-type Ca$^{2+}$ channels 5 µM). Additionally, the retinol effect is significantly less reversible than the farnesol effect. This property affords additional inventive utility in providing and designing long-acting preparations.

According to preferred aspects, structural modifications to enhance the hydrophobicity of the carbons 10 to 12 in the farnesol molecule do not significantly alter the Ca$^{2+}$ channel blocker activity of farnesol, and yet provide longer-acting compounds. Therefore, compound genera based on retinol (e.g., retinol-like or retinol-based farnesol analogues) represent preferred compounds for inhibiting alcohol withdrawal seizures.

Farnesol Analogues Synthesized by Applicants.

Various farnesol analogues were synthesized and tested.

"Cis" Farnesol—

In plants, farnesol comes as a mixture of isomers, including the cis,trans isomer [(2Z,6E)-3,7,11-trimethyldodeca-2,6,10-trien-1-ol, or "cis" farnesol].

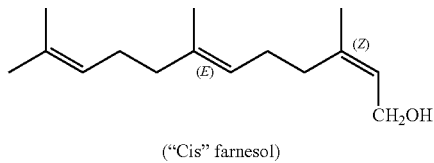 [SMILES: CC(C)=CCC/C(C)=C/CC/C(C)=C\CO]

("Cis" farnesol)

In contrast, all-trans farnesol is the predominant isomer in mammals (Christophe, 1961; Roullet, 1999). Experiments were thus conducted to assess whether the activity of farnesol on Ca$^{2+}$ channels was stereoselective.

Compound Synthesis.

Pure (>98%) "cis" farnesol was obtained by reduction of 2,3-cis-methyl farnesoate with diisobutyl aluminum hydride using standard techniques. The 2,3-cis-methyl farnesoate was obtained by chromatography from a mixture of 2,3-cis- and 2,3-trans-methyl farnesoate (70% trans, 30% cis) kindly provided by Dr. Anderson (Novartis Corporation). The "cis" farnesol was prepared by Patrick McDougal, Ph.D. at Reed College, Portland, Oreg.

Figure 5:
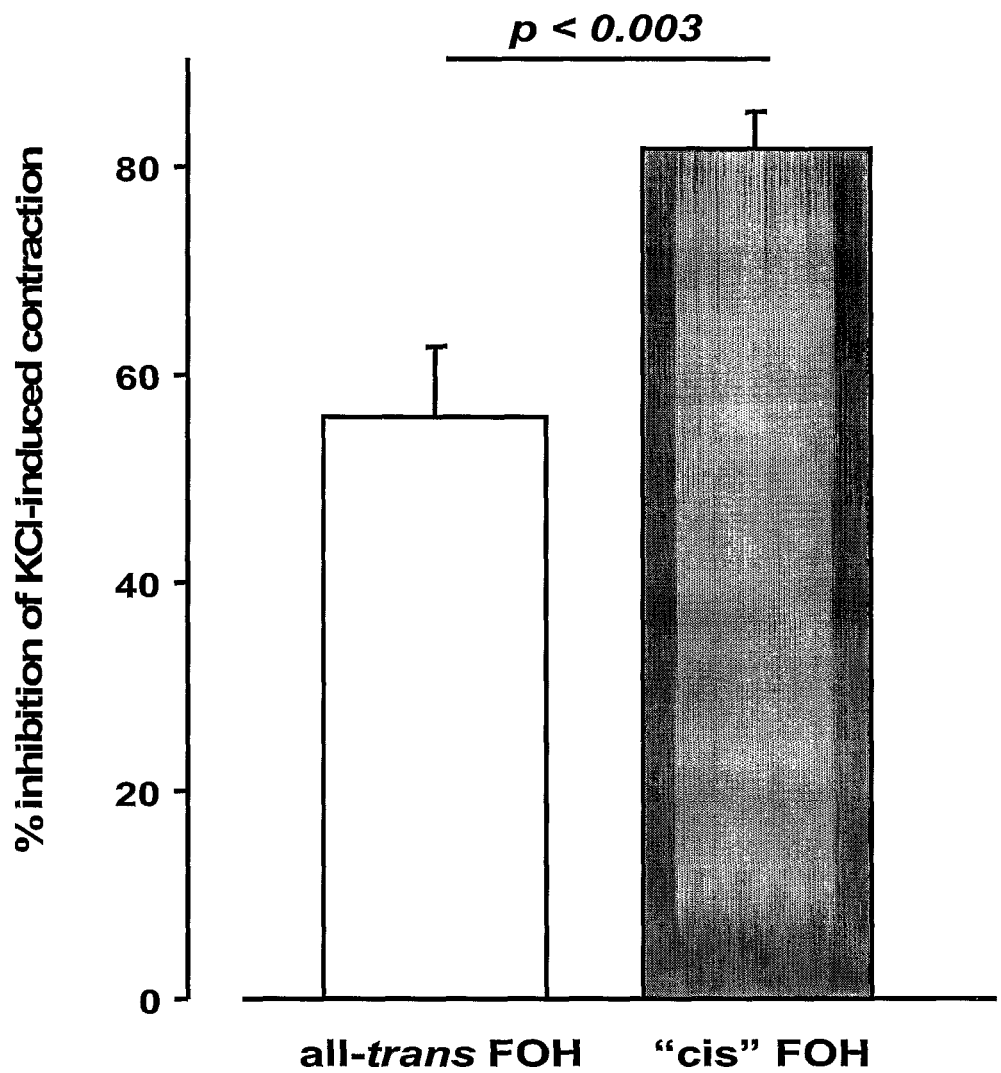
FIG. 5 shows, according to aspects of the present invention, the effects of "cis." and all-trains farnesol on L-type $Ca^{2+}$ channel mediated arterial contraction (mouse mesenteric arteries; mean±SE; n=7/group). "Cis" farnesol was found to be significantly more active on $Ca^{2+}$ channels than all-trans farnesol.

As shown in FIG. 5 (arterial contraction) and FIG. 3 (PC12, Ca$^{2+}$ signaling), "cis" farnesol was significantly more active on Ca$^{2+}$ channels than all-trans farnesol. While it is possible that the "cis" structure confers more activity because of a more favorable interaction with the ion channel, the catalytic efficiency, as observed by applicants, of ADH toward "cis" farnesol is approximately 10-fold lower than that toward all-trans farnesol. Therefore, the greater activity of the "cis" isomer is likely at least in part due to the compounds slower catabolism in situ. Therefore, according to preferred aspects of the present invention, and in view of the data presented herein, "cis" farnesol has a reduced metabolic clearance and a greater or longer action in vivo than all-trans farnesol.

Farnesylamine—

The above-described observation that negatively charged farnesol metabolites (farnesoic acid and farnesyl-PP) are relatively inactive on Ca$^{2+}$ channels (FIG. 2) led us to postulate that positively charged analogues might be more active than farnesol. In this context, farnesylamine [(2E,6E)-3,7,11-trimethyldodeca-2,6,10-trien-1-amine] was evaluates for potential Ca$^{2+}$ channel blocker activity. A method of synthesis was established (see "Methods" EXAMPLE XY) and farnesylamine was tested using applicants' arterial preparation.

Figure 6:
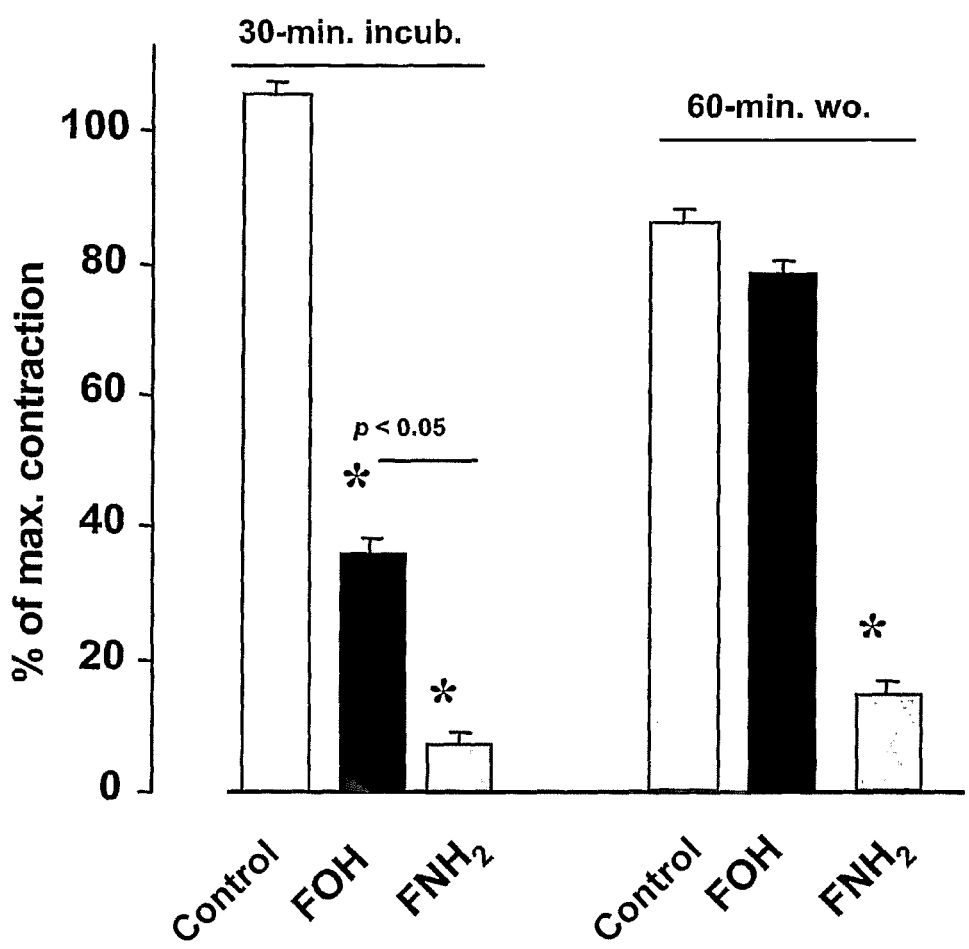
FIG. 6 shows a comparison of the activities of all-trans farnesol and of farnesylamine on L-type $Ca^{2+}$ channel mediated contractions (mouse arteries; mean±SE; all compounds tested at 25 µM). Contractions obtained after 30 min. incubation with the test compounds (left portion of graph), and after a 60-min. wash-out (right portion of graph). The data indicate that farnesylamine is a more potent inhibitor of arterial contractions than farnesol.

The data (FIG. 6) indicate that farnesylamine is a more potent inhibitor of arterial contractions than farnesol. The effect of farnesylamine is relatively less reversible and significant inhibition (~80%) is still observed after extensive wash-out ("60-min. wo"; FIG. 6). Thus, according to preferred aspects of the present invention, farnesylamine is more active than farnesol in vivo and has a more long-lasting effect than the corresponding isoprenol on alcohol withdrawal seizures. Moreover, farnesylamine is likely to be metabolized through pathways different from those involved in farnesol clearance. Indeed, experiments by applicants conducted with rat liver mitochondrial membranes and human recombinant monoamine oxidase A and B, indicate that farnesylamine is a specific substrate for monoamine oxidase A. Without being bound by mechanism, this observation suggests that farnesylamine may compete with endogenous amines in the central nervous system and have significant anti-depressor activity, useful for treating alcoholic patients.

Geranylresorcinol ("GR")—

As discussed above, farnesol is metabolized by intracellular dehydrogenases. Transformation of the hydroxyl group into aldehyde by ADH is likely to follow the steps described for ethanol including: (1) recognition of the alcohol group and nearby atoms by the active site of the enzyme; and (2) transfer of the C1 hydrogen (hydride) atom to NAD$^+$ (ADH cofactor). According to preferred aspects of the present invention, any structural change that would either reduce steric availability of the hydroxyl or prevent hydrogen transfer to NAD$^+$ has the potential to reduce metabolism by ADH; for example, embedding the carbon 1 of the farnesol molecule in a benzene ring to achieve steric hindrance and hydrogen transfer inhibition. Therefore, geranylresorcinol [(E)-3-(3,7-dimethylocta-2,6-dienyloxy)phenol] is a preferred compound. Interestingly, GR has a calculated surface area and volume similar to farnesol (346.28$^{'2}$ vs. 349.29$^{'2}$, and 319.49$^{'3}$ vs. 315.70$^{'3}$ for GR and FOH, respectively), consistent with interacting similarly to farnesol with intracellular targets.

Geranylresorcinol ("GR") was synthesized (see "Methods" EXAMPLE XY) and tested for activity on L-type Ca$^{2+}$ channels. The data obtained showed that GR strongly inhibits KCl-induced arterial contraction and Ca$^{2+}$ signaling (FIG. 2), indicating that GR blocks L-type Ca$^{2+}$ channels and thus, according to preferred aspects of the present invention, has inventive utility for treating alcohol withdrawal seizures. Similar to the results observed with farnesylamine and retinol, the effect of GR is less reversible than that of farnesol, perhaps as a consequence of GR higher octanol-water partition coefficient (C Log P=5.3). Therefore, according to preferred aspects of the present invention, GR has a longer action in vivo as compared to farnesol.

The influence of the GR-specific structural changes on enzyme recognition was examined in separate experiments. The data obtained indicates that GR is a very poor substrate for ADH, and is not recognized by microsomal FolDH. These findings indicate that GR or farnesol analogues with structural elements similar to those present in GR will have pharmacokinetic properties significantly different from those of farnesol, offering yet further compound design options to control drug disposition and efficacy in treating alcohol withdrawal seizures.

Additional Compounds with Activity According to Aspects of the Present Invention; Trifluorofarnesol.

According to particular aspects, fluorination of farnesol in proximity of the hydroxyl group provides increased steric hindrance and reduces hydride formation. Ideally, and by analogy with trifluoroethanol a competitive inhibitor of ADH, fluorination preferably occurs on C2. In farnesol, C2 can accept only one fluorine atom, and C3 can accept none. However, the C3 methyl group can be successfully substituted with a trifluoromethyl group to yield trifluorofarnesol [(Z)-3-(trifluoromethyl)-7,11-dimethyldodeca-2,6,10-trien-1-ol], a precursor in the synthesis of protein farnesyltransferase inhibitors (Dolence, 1996). According to aspects of the present invention, the combined electron-withdrawing effect of the 3 fluor atoms are strong enough to reduce hydride transfer to $NAD^+$ and prevent aldehyde formation. Furthermore, according to additional preferred aspects, because the introduction of a benzene ring nearby the hydroxyl group of farnesol (e.g., "GR") does not affect the $Ca^{2+}$ channel blocker activity of farnesol, the substitution of the C3 methyl with a C3 trifluoromethyl group is similarly tolerated (does not effect $Ca^{2+}$ channel blocker activity). Therefore, according to preferred aspects of the present invention, trifluorofarnesol has significant activity on $Ca^{2+}$ channels, and is a poor ADH substrate. Therefore, according to preferred aspects of the present invention, trifluorofarnesol is a preferred farnesol analogue with substantial antiseizure activity and reduced metabolic clearance.

Example 4

Synthesis and Purification Methods for Farnesylamine, Geranylresorcinol (GR), Cis,Trans Farnesol and Fluorinated Farnesol This Example describes, according to aspects of the present invention, synthesis and purification methods for farnesylamine, geranylresorcinol, cis,trans farnesol and fluorinated farnesol (e.g., ~0.5 g each). Specific procedures yield milligram amounts of pure (>98.0%) products. Trifluorofarnesol is synthesized using art-recognized standard published procedures "Cis" Farnesol—Synthesis and Analysis of (2Z,6E)-3,7,11-trimethyldodeca-2,6,10-trien-1-ol ("Cis" Farnesol)

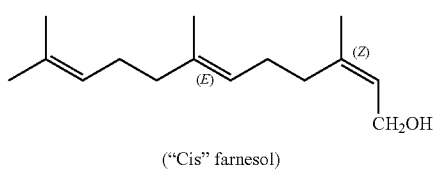 [SMILES: CC(C)=CCC/C(C)=C/CC/C(C)=C\CO]

("Cis" farnesol)

According to the present invention, a mixture of 2,3-cis- and 2,3-trans-ethyl farnesoate is obtained from a Wittig-type reaction on commercially available trans-geranylacetone. The cis/trans isomers are easily separated by chromatography. The pure 2,3-cis-ethyl farnesoate provides the precursor to 2,3-cis farnesol via reduction with diisobutyl aluminum hydride.

This reaction produces no unwanted double bond isomers. Analysis by $^1$HNMR spectroscopy easily distinguishes between the cis and trans forms of farnesoic esters. The most diagnostic protons are the allylic protons at C4, and the vinyl proton at C6. In the cis form these protons are shifted downfield relative to their trans counterparts. This is most noticeable for the C4 allylic protons which appear 0.4-0.6 ppm downfield from the C4 trans protons. This is consistent with those protons being cis to the carbonyl group and thus residing in the deshielding region of the carbonyl group. A similar, albeit smaller effect, is seen for the C6 vinyl proton which is seen about 0.1 ppm downfield in the cis isomers. These shift differences allow for the unambiguous assignment of cis and trans stereochemistry. The purity of the isomers can also be assessed by integration of the appropriate regions. Preferably, NMR spectroscopy is performed on, for example, a Brücker 400 NMR spectrometer. Purity is alternatively or additionally checked by GC/MS.

Farnesylamine—Synthesis and Analysis of (2E,6E)-3,7,11-trimethyldodeca-2,6,10-trien-1-amine (Farnesylamine)

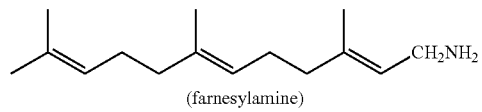

(farnesylamine)

According to the present invention, farnesylamine is prepared essentially as described by Sen & Roach, (Sen, 1995) with modifications. Sen's method has the advantage of leading to a single product by avoiding the otherwise competing allylic substitution and thus producing only farnesylamine. Briefly, t-,t-farnesol is reacted with triphenylphosphineoxyde to obtain t-,t-farnesylphthalimide (~76% yield). Cleavage of the phthalimide is done by Sen's procedure, but isolation of the final product is preferably by distillation instead of chromatography. The yield of this step is about 25%. Preparations of farnesylamine of a purity ≥99% and identity confirmed by $^{1H}$NMR spectroscopy can be obtained.

Geranylresorcinol—Synthesis and Analysis of (E)-3-(3,7-dimethylocta-2,6-dienyloxy)phenol (Geranylresorcinol)

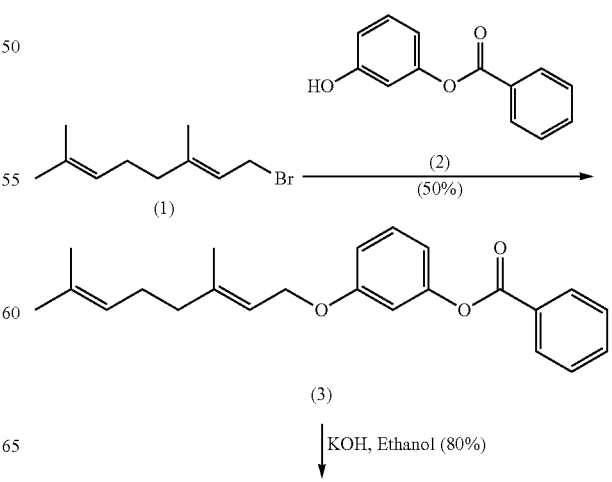

-continued

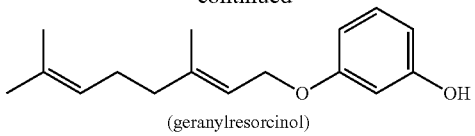
(geranylresorcinol)

According to the present invention, the synthesis of geranylresorcinol (GR) (4) is based on the condensation of geranyl bromide (1) and 3-hydroxyphenyl benzoate (2), followed by alkaline cleavage of the formed ester (3). The method generates pure GR with an overall yield of 40%. The compound is stable when stored at −20° C. either in its pure form or in ethanol solutions (typically prepared at 25 mM). Long-term storage may be associated with some darkening of the product, as typically observed with electron-rich phenols, but it is not associated with significant loss of activity (on arteries).

Trifluorofarnesol—Synthesis and Analysis of (2E, 6E)-,7,11-dimethyl-3-(trifluoromethyl)dodeca-2,6, 10-trien-1-ol (Trifluorofarnesol)

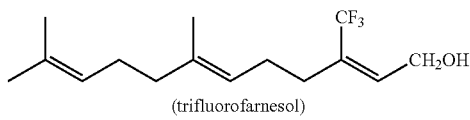
(trifluorofarnesol)

According to the present invention, trifluorofarnesol is prepared essentially as described by Dolence and Poulter (Dolence, 1996). The synthesis involves: (1) condensation of ethyl 4,4,4-trifluoooacetoacetate with geranyl bromide; (2) decarboxylation of the product with lithium chloride in aqueous DMF to give a trifluoroketone; (3) conversion of the ketone to the ester by a Horner-Emmons Wittig reaction using triethylphosphonoacetate; and (4) reduction of the ester using diisobutyl aluminum hydride to afford trifluorofarnesol. The Z isomer is separated by silica gel chromatography (Dolence, 1996).

Example 5

Determining Effects of Farnesol Analogues on Withdrawal Seizures in Alcohol-Dependent Mice According to the present invention, the anti-alcohol withdrawal seizure activity of the farnesol analogues is evaluated using the DBA/2J mouse model of severe alcohol withdrawal (males only, ~25 g BW and the HIC scoring method described above in EXAMPLE 2. The activity of these compounds is compared to the activity of farnesol administered at the same dose. The details of the model and the HIC scoring method will not be repeated. However, several issues need to be presented in this section.

Farnesol Analogues: Origin, Dose, Formulation and Injection—Origin:
"cis" farnesol, GR, trifluorofarnesol and farnesylamine are obtained as described under EXAMPLE 4 herein above. All-trans farnesol and the other analogues are purchased from commercial sources: trans-nerolidol (e.g., 95% pure; Aldrich, cat. #33, 525-8), all-trans retinol (e.g., >99%; Fluka, cat. #: 95144), and all-trans farnesol (e.g., ~97%; Fluka, cat. #: 46193).

Dose—
The activities of the farnesol analogues on seizures are assessed at a dose equivalent to the dose of farnesol that gives approximately a 50% inhibition of the HIC score in dependent DBA/2J mice. Preferably, a dose of 300 mg/kg suppresses almost completely HICs in withdrawing animals, whereas a dose of 200 mg/kg induces a 56% inhibition only. Preferably, no effect of farnesol is observed at 50 mg/kg. Preferably, all analogues are tested at a dose of 200 mg/kg, and pilot doses are preferably used to determine the best dose for each compound.

Formulation and Injection—
Preferably, all compounds are prepared as emulsions in saline-BSA (3 g/l) using a Branson sonicator set at '3" for 30 s (50% cycle). Sonication is performed in an ice bath to minimize unwanted degradation of the compounds. Suspensions are injected i.p. using 27-G needles and "tuberculin-type" syringes. All-trans retinol is very sensitive to light, as is appreciated in the art. Thus, retinol suspensions are prepared and kept in the dark until use, and the syringes used for injection are wrapped in aluminum foil.

Injection Schedule—
Preferably, test compounds are injected 4 hours after withdrawal from the alcohol chambers. Seizures in DBA/2J mice reach their maximum intensity by hour 4 post withdrawal. This time, therefore, gives the best (greatest) HIC score range (ethanol- vs. air-breathing animals) to evaluate inhibition by the compounds.

HIC Measurement Time Course—
Preferably, HIC scoring is performed hourly before injection, 10, 20, 30, 40 and 60 minutes after drug injection, and then hourly until the 10-hour time point. The animals are again scored the next day 24 and 25 hours post withdrawal.

Outcome Measures—
Preferably, the following four parameters are calculated from the HIC score data and are used to compare the test compounds with each other or with all-trans farnesol:

peak score inhibition, defined as the ratio of the largest HIC score difference between drug-treated, ethanol-breathing animals and vehicle-treated, ethanol-breathing animals, to the HIC score difference between vehicle-treated, ethanol-breathing animals and vehicle-treated, air-breathing animals, at matching time point;

time to peak inhibition, defined as the average time it takes for a test compound to reach peak inhibition after injection;

duration of action, defined as the difference between injection time and time at which the HIC score curves of the drug-treated, ethanol breathing animals crosses the score curves of the vehicle-treated, ethanol breathing group (end-of-action time point); and Total inhibition (area under the curve), defined as the HIC score integrated from injection time to end-of-action time point. In case the effect of a compound lasts beyond the 10-h time point, or is still present 24 or 25 hours post-withdrawal, these time points and associated scores will be used in the integration process.

Number of Animals and Statistical Analysis—
Preferably, each group has a minimum of 12 animals. Such a relatively large 'n' is necessary to offset the natural variation of the convulsion scores in the animals exposed to alcohol. Group values are preferably presented as mean±SE. Drug effect is preferably estimated using analysis of variance for repeated measures with the customary $p \leq 0.05$ level of significance. Statistical analyses is preferably performed using the Statgraphics Plus software (version 5.1, Professional edition).

Side-Effects—

Preferably, the animals are observed for unusual behavior (lethargy, spontaneous convulsions) before each HIC scoring. Death is noted.

Example 6

Evaluating the Activity of Farnesol Analogues on Voltage-gated L- and N-type Ca+ Channels According to preferred aspects of the present invention, anti-alcohol withdrawal seizure activity in vivo is dependent on neuronal voltage-gated, L- and N-type $Ca^{2+}$ channel inhibition. Preferably a comparison of L-type and N-type $Ca^{2+}$ channel-specific $IC_{50}$ for each compound in comparison with all-trans farnesol is performed.

Preferably, such comparison are accomplished by measuring the inhibitory activity of the compounds tested at different concentrations, on KCl-induced $Ca^{2+}$ signaling in NGF-differentiated PC12 cells. PC12 cells are preferably cultured with NGF to induce the neuronal phenotype and the expression of voltage-gated L-type, N-type and P/Q type $Ca^{2+}$ channel (Solem, 1997). The activity of the $Ca^{2+}$ channels is preferably determined by measuring the intensity of intracellular $Ca^{2+}$ signals following plasma membrane depolarization with high extracellular KCl concentration (see e.g., Solem, 1997; Roullet, 1997, 1999b). The activity of L-type $Ca^{2+}$ channel activity is specifically determined after block of the N-type $Ca^{2+}$ channels with ω-conotoxin GVIA and block of the P/Q type $Ca^{2+}$ channels with ω-agatoxin IVA. The activity of the N-type $Ca^{2+}$ channels is determined after block of the L-type $Ca^{2+}$ channels with nifedipine and block of the P/Q type $Ca^{2+}$ channels with ω-agatoxin IVA.

Methods—Cell Culture—

PC12 cells are preferably grown in plastic Petri dishes containing DMEM supplemented with 15% (v/v) heat-inactivated horse serum and a mixture of penicillin and streptomycin. Calcium channel expression is preferably induced by culture with 50 ng/ml of NGF for 7 days (Solem, 1997).

Measurement of Intracellular $Ca^{2+}$—

Preferably, after NGF induction, cells are trypsinized and loaded with fura-2 as previously described (Roullet, 1995, 1997). $Ca^{2+}$ signals are preferably measured in cells in suspension, using, for example, a dual-wavelength spectrofluorometer (F-2000 Hitachi). Excitation will, for example, alternate between 340 nm and 380 nm and emission will be recorded at 510 nm (Grynkiewicz, 1985). Calibration of the fura-2 fluorescence signal is preferably performed with ionomycin (Rmax) and Tris-EGTA (Rmin), using a fura-2/$Ca^{2+}$ dissociation constant of 190 nM (Solem, 1997). $Ca^{2+}$ signals are defined as the difference between basal intracellular free $Ca^{2+}$ concentration (typically 20-50 nM) and peak intracellular free $Ca^{2+}$ concentration obtained after rapid addition of 50 mM KCl to the cell suspension. To block L-type $Ca^{2+}$ channels, the cells are preferably incubated with 1 μM nifedipine for 5 min. before $Ca^{2+}$ measurements. To block N-type and P/Q type $Ca^{2+}$ channels, we will use 1 mM ω-conotoxin and 300 nM ω-agatoxin.

Addition of Drugs—

Each compound are preferably tested at concentrations ranging from 0 (vehicle) to 25 μM (0.1, 0.5, 1.0, 2.0, 5.0, 10 and 25 μM). Preferably, for experiments to determine IC50s on L-type $Ca^{2+}$ channels, each drug is added to the cells 2 minutes prior addition of KCl. Because inhibition of N-type $Ca^{2+}$ channels by farnesol is frequency-dependent (open-channel and inactivated-channel block, Roullet, 1999), a more complex design is preferably used for the experiments to determine $IC_{50}$s on N-type $Ca^{2+}$ channels. The cells are first incubated for 5 minutes in a 50 mM KCl buffer containing the test compound and both nifedipine and ω-agatoxin. The presence of high KCl concentrations opens and inactivates N-type $Ca^{2+}$ channels, and also facilitates inhibition by farnesol or analogues. The cells are then quickly rinsed by centrifugation (~2 min.) and resuspended in a 5 mM buffer also containing the test compound, the toxin and nifedipine. After baseline recording, the cells are depolarized again with 50 mM KCl. This design is similar to that described by Solem and colleagues, and is preferably used to maximize the effect of farnesol analogues on N-type $Ca^{2+}$ channels.

Data Analysis—

Preferably, a minimum of 6 data points (2 batches of cells) per drug concentration are collected. $IC_{50}$ are preferably estimated using non-linear curve fitting and, for example, the Microsoft™ Excel Solver add-in.

Use of the Animals—

To be able to determine the effect of the test compounds on seizures it is necessary to use animals. Preferably, the number of animals is minimized based on the statistics of the experiments. Preferably, the number of animals used is reduced to the smallest number possible to obtain detectable and significant differences. Preferably, DBA/2J mice are used. Half of the animals are exposed to alcohol vapor for 3 days before receiving the test compounds. The other half are used as control, 'air-breathing' subjects. Injections are preferably performed intraperitoneally.

Veterinary Care—

Animals are housed and cared for according to the guidelines of the Public Health Service Policy of Humane Care and Use of Laboratory Animals. Animal comfort is ensured by frequent changing of the bedding material, regular feeding and water and fixed light cycles, temperature and humidity of the animal quarters. All experimental procedures are approved by the respective Research Institution Animal Care Committee prior to performing the research. Preferably, the facility is an AAALAC approved facility under the direction of a full time veterinarian assisted by a staff that includes 2 other full time veterinarians.

Reduction of Stress and Discomfort of the Animals—

In all cases discomfort, distress and pain or injury is held to the minimum necessary to accomplish the goals of the proposed research.

Method of Euthanasia—

Preferably, if the animals show intense pain or suffering during the experimental period, they will be euthanized according to procedures approved by the Research institution.

Example 7

Treatment of Convulsive Seizure

The preceding examples show that isoprenoid-based compounds (e.g., farnesol and/or farnesol analogues or derivatives) or dehydroisoprenoid-based compounds provide novel compositions and methods for treatment of AWS, and in particular alcohol withdrawal seizures.

Additionally, according to the present applicant, preferred aspects of the present invention provide a method of treating convulsive seizure, comprising administering to a subject in need thereof a therapeutically effective amount of a isoprenoid-based compound (e.g., farnesol compound) or dehydroisoprenoid-based compound, wherein the convulsive seizure is non-alcohol related.

In particular aspects, the convulsive seizure is selected from the group consisting of: partial epileptic seizures; generalized epileptic seizures; absence seizures; myoclonic seizures; clonic seizures; tonic seizures; tonic-clonic seizures; atonic seizures; pseudoepileptic or non-epileptic seizures caused by cardiovascular disease, toxic or metabolic disorders including hypoglycemia and drug toxicity, or sleep disorders; non-epileptic seizures induced by psychiatric conditions including hysteria and schizophrenia; convulsions or seizures caused by acquired immunodeficiency syndrome (AIDS), Parkinson's disease, Alzheimer's disease, other neurodegenerative disease including Huntington's chorea, schizophrenia, obsessive compulsive disorders, tinnitus, neuralgia, trigeminal neuralgia, post-traumatic epilepsy, intoxication or withdrawal from barbiturates, brain illness or injury, brain tumor, choking, drug abuse, electric shock, fever, head injury, heart disease, heat illness, high blood pressure, meningitis, poisoning, stroke, toxemia of pregnancy, uremia related to kidney failure, venomous bites and stings, withdrawal from benzodiazepines, febrile convulsions, and afebrile infantile convulsions.

Most preferably, the convulsive seizure is a partial or generalized epileptic seizure.

In particularly preferred aspects, the farnesol compound is selected from the group consisting of: (2E,6E)-3,7,11-trimethyldodeca-2,6,10-trien-1-ol (all-trans farnesol); (2Z,6E)-3,7,11-trimethyldodeca-2,6,10-trien-1-ol (cis-farnesol); (E)-3,7,11-trimethyldodeca-1,6,10-trien-3-ol (nerolidol); (2E, 6E)-3,7,11-trimethyldodeca-2,6,10-trien-1-amine (farnesylamine); (E)-3-(3,7-dimethylocta-2,6-dienyloxy) phenol (geranylresorcinol); (2E,6E)-,7,11-dimethyl-3-(trifluoromethyl)dodeca-2,6,10-trien-1-ol (trifluorofarnesol); and (2E,4E,6E,8E)-3,7-dimethyl-9-(2,6,6-trimethylcyclohex-1-enyl)nona-2,4,6,8-tetraen-1-ol (all-trails retinol).

Preferably, the subject is human. Preferably, the farnesol compound is administered from 1 to 3 times per day. Preferably, administration is via pulmonary delivery. Preferably, pulmonary delivery is via intranasal delivery of at least one of an aerosolized composition, and a nebulized composition.

LITERATURE CITED

Altamura A C, Regazzetti M G, Porta M. Nimodipine in human alcohol withdrawal syndrome—an open study. *Eur Neuropsychopharmacol* 1990; 1:37-40.

Banger M, Benkert O, Roschke J, Herth T, Hebenstreit M, Philipp M, Aldenhoff J B. Nimodipine in acute alcohol withdrawal state. *J Psychiatric Res* 1992; 26:117-123.

Bayard M, McIntyre J, Hill K, Woodside J. Alcohol withdrawal syndrome. *Am Fam Physician* 2004; 69:1443-50

Bentinger M, Grunler J, Peterson E, Swiezewska E, Dallner G. Phosphorylation of farnesol in rat liver microsomes: properties of farnesol kinase and farnesyl phosphate kinase. *Arch Biochem Biophys* 1997; 353:191-198.

Binet L, Binet P, Miocque M, Morin H, Pechery C, Roux M. Le farnésol, substance psycho-sédative et spasmolytique. *Thérapie* 1972; 27:893-905.

Binet L, Binet P, Miocque M, Roux M, Bernier A. Recherche sur les propriétes pharmacodynamiques (action sédative et action spasmolytique) de quelques alcohols terpéniques aliphatiques. *Annales Pharmaceutiques Française* 1972; 30:611-616.

Binet P, Miocque M, Roux M, Rinjard P. Farnésol et neuroleptiques. I. Renforcement par le farnésol de l'effet cataleptigene expérimental des neuroleptiques. *Annales Pharmaceutiques Française* 1975; 33:229-234.

Binet P, Miocque M, Roux M, Rinjard P. Farnesol et neuroleptiques. II. Action du farnésol, seul ou associé à un neuroleptique, sur les stéréotypies provoquées chez le Rat par l'amphétamine. *Ammales Pharmaceutiques Française* 1975; 33:321-328.

Binet P. Action quelques alcohols terpéniques sur le système nerveux des poissons. *Annales Pharmaceutiques Française* 1972; 30:653-658.

Bone G H, Majchrowicz E, Martin P R, Linnoila M, Nutt D J. A comparison of calcium antagonists and diazepam in reducing ethanol withdrawal tremors. *Psychopharinacology* 1989; 99:386-388.

Brennan C H, Crabbe J, Littleton J M. Genetic regulation of dihydropyridine-sensitive calcium channels in brain may determine susceptibility to physical dependence on alcohol. *Neuropharmacology* 1990; 29:429-432.

Brennan C H, Littleton J M. Chronic exposure to anxiolytic drugs, working by different mechanisms causes up-regulation of dihydropyridine binding sites on cultured bovine adrenal chromaffin cells. Neuropharmacology 1991; 30:199-205

Buck K, Metten P, Belknap J, Crabbe J. Quantitative trait loci affecting risk for pentobarbital withdrawal map near alcohol withdrawal loci on mouse chromosomes 1, 4, and 11. *Mammalian Genome* 1999; 10:431-437

Buck K J, Metten P, Belknap J K, Crabbe J C. Quantitative trait loci involved in genetic predisposition to acute alcohol withdrawal in mice. *J Neuroscience* 1997; 17:3946-3955.

Chang P H, Steinberg M B. Alcohol withdrawal. *Med Clin North Am* 2001; 85:1191-1212

Christopher J, Popjak G. Studies on the biosynthesis of cholesterol: XIV. The origin of prenoic acids from allyl pyrophosphates in liver enzyme systems. *J Lipid Res* 1961; 2:244-257.

Crabbe J C, Young Jr. E R, Kosobud A (1983). Genetic correlations with ethanol withdrawal severity. *Pharmacol Biochem Behav* 1983; 18(Suppl. 1):541-547.

Crabbe J C. Sensitivity to ethanol in inbred mice: genotypic correlations among several behavioral responses. *Behav Neurosci* 1983; 97:280-289

Crabbe J C, Merrill C, Belknap J K. Acute dependence on depressant drugs is determined by common genes in mice. *J Pharmacol Exp Ther* 1991; 257:663-667

Crabbe J C, Belknap J K, Buck K J, Metten P. Use of recombinant inbred strains for studying genetic determinants of responses to alcohol. *Alcohol & Alcoholism* 1994; S2:67-71.

Crabbe J C, Belknap J K, Metten P, Grisel J E, Buck K J. Quantitative trait loci: mapping drug and alcohol-related genes. *Adv Pharmacol* 1998; 42:1033-1037

Crabbe, J. C. (1998). "Provisional mapping of quantitative trait loci for chronic ethanol withdrawal severity in BXD recombinant inbred mice." *J Pharmacol Exp Ther* 286(1): 263-271.

Crews F T. Morrow A L. Criswell H. Breese G. Effects of ethanol on ion channels. *Int Rev Neurobiol* 1996; 39:283-367.

Davies M. The role of GABAA receptors in mediating the effects of alcohol in the central nervous system. *J Psychiatr Neurosci* 2003; 28:263-274

DeLima J G, Xue H, Phanouvong T, Colburn L, McCarron D A, Bennett W M, Roullet J-B. In vivo and in vitro effect of FK506 in rat and human arteries. *Kidney Int.*, 1999; 55:1518-1527.

Diamond I, Gordon A S. Cellular and molecular neuroscience of alcoholism. *Physiol. Rev.* 1997; 77:1-20

Dolence J M, Poulter C D. Synthesis of analogues of farnesyl diphosphate. *Tetrahedron* 1996; 52:119-130

Ertel E A, Campbell K P, Harpold M M, Hofmann F, Mori Y, Perez-Reyes E, Schwartz A, Snutch T P, Tanabe T, Bimbaumer L, Tsien R W, Catterall W A. Nomenclature of voltage-gated calcium channels. *Neuron* 2000; 25:533-535.

Fehr C, Shirley R L, Belknap J K, Crabbe J C, Buck K J. Congenic mapping of alcohol and pentobarbital withdrawal liability loci to a <1 centimorgan interval of murine chromosome 4: identification of Mpdz as a candidate gene. *J Neuroscience* 2002; 22:3730-3738.

Goldstein D B. An animal model for testing effects of drugs on alcohol withdrawal reactions. *J Pharmacol Exp Ther* 1972; 183:14-22.

Grynkiewicz, G, Poenie M, Tsien R Y. A new generation of $Ca^{2+}$ indicators with greatly improved fluorescence properties. *J Biol Chem* 1985; 260:3440-3450.

Guppy L J, Crabbe J C, Littleton J M. Time course and genetic variation in the regulation of calcium channel antagonist binding sites in rodent tissues during the induction of ethanol physical dependence and withdrawal. *Alcohol Alcoholism* 1995; 30:607-615

Hall A C, Lieb, W R, Franks N P. Isensitivity of P-type calcium channels to inhalational and intravenous general anesthetics. *Anesthesiology* 1994; 81:117-123

Han C L, Liao C-S, Wu C-W, Hwong C L, Lee A R, Yin S J. Contribution to first-pass metabolism of ethanol and inhibition by ethanol for retinol oxidation in the human alcohol dehydrogenase family. *Eur. J. Biochem.* 1998; 254:25-31

Harper J C, Brennan C H, Littleton J M. Genetic up-regulation of calcium channels in a cellular model of ethanol dependence. Neuropharmacology 1989; 28:1299-1302

Hell J W. Westenbroek R E. Warner C. Ahlijanian M K. Prystay W. Gilbert M M. Snutch T P. Catterall W A. Identification and differential subcellular localization of the neuronal class C and class D L-type calcium channel alpha 1 subunits. *J Cell Biol* 1993; 123:949-962.

Hoffman P L. NMDA receptors in alcoholism. *Int Rev Neurobiol* 2003; 56:35-82.

Jarvis S, Chantabouly T, Burlingame P, McDougal P, Zamponi G W, Roullet J-B. Dihydropyridine-sensitive calcium signaling in PC12 cells: regulation by the farnesol pathway. *Society for Neuroscience,* 29th Annual Meeting, Miami Beach, Fla., Oct. 23-28, 1999

Keung W-M. Human liver alcohol dehydrogenases catalyze the oxidation of the intermediary alcohols of the shunt pathway of mevalonate metabolism. *Biochem. Biophys. Res. Commun.* 1991; 174:701-707

Kosobud A E, Crabbe J C. Genetic influences on the development of alcohol physical dependence and withdrawal. In *The Genetics of Alcoholism* (Eds: H Begleiter and B Kissin), 221-256. Oxford University Press, Oxford, United Kingdom, 1995.

Lipscombe D. Pan J Q. Gray A C. Functional diversity in neuronal voltage-gated calcium channels by alternative splicing of Ca(v) alpha1. *Mol Neurobiol* 2002; 26:21-44.

Litten R Z, Allen J P. Pharmacotherapies for alcoholism: promising agents and clinical issues. *Alcohol Clin Exp Res* 1991; 15:620-633

Little H J, Dolin S J, Hlasey M J. Calcium antagonists decrease the ethanol withdrawal syndrome. *Life Sci* 1986; 39:2059-2065

Littleton J M, Little H J, Whittington M A. Effects of dihydropyridine calcium channel antagonists in ethanol withdrawal: doses required, stereospecificity and actions of Bay K 8644. *Psychopharmacology* 1990; 100:387-392.

Luft U, Bychkov R, Gollasch M, Gross V, Roullet J-B, McCarron D A, Ried C, Hofmann F, Yagil Y, Yagil C, Haller H, Luft F C. Farnesol blocks the L-type $Ca^{2+}$ channel by targeting the $\square_{1C}$ subunit. *Arterioscler Thromb Vasc Biol* 1999; 19:959-966.

Mayo-Smith M F, Cushman P, Hill A J, Jara G, Kasser C, Kraus M, Nauts D, Saitz R, Smith J W, Sulliva J, Thiessen N. Pharmacological management of alcogol withdrawal: a meta-analysis and evidence-based practice guideline. *JAMA* 1997; 278: 144-151.

McMahon T, Andersen R, Metten P, Crabbe J C, Messing R O. Protein kinase C $\square$ mediates up-regulation of N-type calcium channels by ethanol. *Mol Pharmacol* 2000; 57:53-58

Messing R O, Carpenter C L, Diamond I, Greenberg D A. Ethanol regulates calcium channels in clonal neural cells. *Proc Natl Acad Sci USA,* 1989; 83:6213-6215.

Metten P, Crabbe J C. Common genetic determinants of severity of acute withdrawal from ethanol, pentobarbital, and diazepam in inbred mice. *Behavioural Pharmacology* 1994; 5:533-547.

Metten P, Crabbe J C. Dependence and Withdrawal. In *Pharmacological Effects of Ethanol on the Central Nervous System.* R. A. Deitrich and V. G. Erwin, Editors. CRC Press, Boca Raton, Fla., CRC Press, pp. 269-290, 1996

Metten P, Belknap J K, Crabbe J C. (1998). "Drug withdrawal convulsions and susceptibility to convulsants after short-term selective breeding for acute ethanol withdrawal." *Behav Brain Res* 1998; 95:113-22.

Metten P, Crabbe J C. Genetic determinants of severity of acute withdrawal from diazepam in mice: commonality with ethanol and pentobarbital. *Pharmacol Biochem Behav* 1999; 63:473-479

Mohri Y, Katsura M, Shuto K, Tsujimura A, Ishii R, Ohkuma S. L-type high voltage-gated calcium channels cause an increase in diazepam binding inhibitor mRNA expression after sustained exposure to ethanol in mouse cerebral cortical neurons. Brain Res Mol Brain Res 2003; 113:52-56.

Moreno Davila H. Molecular and functional diversity of voltage-gated calcium channels. *Annals of the New York Academy of Sciences.* 868:102-17, 1999 Apr. 30.

Mullikin-Kilpatrick D, Mehta N D, Hildebrandt J D, Treistman S N. Gi is involved in ethanol inhibition of L-type calcium channels in undifferentiated but not differentiated PC-12 cells. *Mol Pharmacol* 1995; 47: 997-1005.

Myrick H, Anton R F. Treatment of alcohol withdrawal. *Alcohol Health Res World* 1998; 22:38-43

N'Gouemo P, Morad M. Ethanol withdrawal seizure susceptibility is associated with upregulation of L- and P-type $Ca^{2+}$ channel current in rat inferior colliculus neurons. Neuropharmacology 2003; 45:429-437.

Roullet J-B, Xue H, Pappu A S, Roullet C, Holcomb S, McCarron D A. Mevalonate availability and cardiovascular functions. *Proc Natl Acad Sci, USA* 1993; 90:11728-11732

Roullet J-B, Xue H, Roullet C H, Fletcher W S, Cipolla M J, Harker C T, MCarron D A. Mevalonate availability affects human and rat resistance vessel function. *J Clin Invest* 1995; 96:239-244.

Roullet J-B, Xue H, Chapman J, McDougal P, Roullet C M, McCarron D A. Farnesyl analogues inhibit vasoconstriction in animal and human arteries. *J Clin Invest* 1996; 97:2384-2390.

Roullet J-B, Le Quan Sang K H, Luft U, McCarron D A, Devynck M A. Farnesol, a potent inhibitor of vasoconstriction, decreases vascular smooth muscle cell $Ca^{2+}$ uptake without affecting membrane fluidity. *J Hypertens* 1997a; 15:1723-1728

Roullet J-B, Luft U C, Xue H, Chapman J, Bychov R, Roullet C M, Luft F C, Haller H, McCarron D A. Farnesol inhibits L-type $Ca^{2+}$ channels in vascular smooth muscle cells. *J Biol Chem* 1997b; 272:32240-32246

Roullet J-B, Spaetgens R L, Burlingame T, Zamponi G W. Modulation of presynaptic calcium channels by the mevalonate pathway. *J Biol Chem*, 1999; 274:25439-25446.

Saitz R, O'Malley S S. Pharmacotherapies for alcohol abuse. Withdrawal and treatment. *Medical Clinics of North America* 1997; 81:881-907.

Sen S E, Roach S. A convenient two-step procedure for the synthesis of allylic amines from alcohols. *Synthesis* 1995: 756-758

Shulman A, Jagoda J, Laycock G, Kelly H. Calcium channel blocking drugs in the management of drug dependence, withdrawal and craving. A clinical pilot study with nifedipine and verapamil. *Australian Family Physician* 1998; 27:S19-24.

Solem M, McMahon T, Messing R O. Protein kinase A regulates the inhibition of N- and P/Q-type calcium channels by ethanol in PC12 cells. *J Pharmacol Exp Ther,* 1997; 282:1487-1495

Victor M, Brausch C. The role of abstinence in the genesis of alcoholic epilepsy. *Epilepsy* 1967; 8:1-20.

Waller G R Dehydrogenation of trans,trans farnesol by horse liver alcohol dehydrogenase. *Nature* 1965; 207; 1389-1390

Walter H J, Messing R O. Regulation of neuronal voltage-gated calcium channels by ethanol. *Neurochem Int* 1999; 35:95-101

Wang X, Lemos J R, Dayanthi G, Nordmann J J, Treitsman S N. Ethanol reduces vasopressin release by inhibiting calcium currents in nerve terminals. *Brain Res* 1991; 551:339-341

Wang X-D. Chronic alcohol intake interferes with retinoid metabolism and signaling. *Nutr Rev* 1998; 57:51-59.

Watson W P. Little H J. Selectivity of the protective effects of dihydropyridine calcium channel antagonists against the ethanol withdrawal syndrome. *Brain Res* 2002; 930: 111-122.

Westfall D, Aboushadi N, Shackelford J E, Krisans S K. Metabolism of farnesol: phosphorylation of farnesol by rat liver microsomal and peroxisomal fractions. *Biochem Biophys Res Commun* 1997; 230:562-568

Whittington M A, Little H J. A calcium channel antagonist stereoselectively decreases ethanol withdrawal hyperexcitability but not that due to bicuculline, in hippocampal slices. *Br J Pharmacol* 1991a; 103:1313-1320

Whittington M A, Dolin S J, Patch T L, Siarey R J, Butterworth A R, Little H J. Chronic dihydropyridine treatment can reverse the behavioral consequences of and prevent adaptations to chronic ethanol treatment. *Br J Pharmacol* 1991b; 103:1669-1676

Whittington M A, Little H J. Changes in voltage-operated calcium channels modify ethanol withdrawal hyperexcitability in mouse hippocampal slices. *Exper Physiol* 1993; 78:347-370

The invention claimed is:

1. A method for the treatment of alcohol withdrawal syndrome, comprising administering to a subject in need thereof a therapeutically effective amount of a compound selected from the group consisting of
(E)-3,7,11-trimethyldodeca-1,6,10-trien-3-ol,
(2E,6E)-3,7,11-trimethyldodeca-2,6,10-trien-1-amine,
(E)-3-(3,7-dimethylocta-2,6-dienyloxy)phenol, and
(2E,6E)-7,11-dimethyl-3-(trifluoromethyl)dodeca-2,6,10-trien-1-ol,
or a pharmaceutically acceptable salt, ester or amide of said compound.

2. The method of claim 1, wherein the compound is (E)-3,7,11-trimethyldodeca-1,6,10-trien-3-ol.

3. The method of claim 1, wherein the compound is (2E,6E)-3,7,11-trimethyldodeca-2,6,10-trien-1-amine.

4. The method of claim 1, wherein the compound is (E)-3-(3,7-dimethylocta-2,6-dienyloxy)phenol.

5. The method of claim 1, wherein the compound is (2E,6E)-7,11-dimethyl-3-(trifluoromethyl)dodeca-2,6,10-trien-1-ol.

6. The method of claim 1 wherein the treatment of alcohol withdrawal syndrome comprises treating at least one symptom selected from the group consisting of tremor, anxiety, autonomic hyperactivity, sweating, increased blood pressure, tachycardia, hallucinations, alcohol withdrawal seizures and delirium tremens.

7. The method of claim 6 wherein the at least one symptom is treating alcohol withdrawal seizures.

8. The method of claim 6 wherein the at least one symptom is treating delirium tremens.

9. The method of claim 1 wherein the subject is human.

10. The method of claim 1 wherein administration is via intranasal delivery of at least one of an aerosolized composition, and a nebulized composition.

11. The method of claim 1 wherein administration is via pulmonary delivery.

12. The method of claim 11, wherein pulmonary delivery is via intranasal delivery of at least one of an aerosolized composition, and a nebulized composition.

13. The method of claim 1 wherein the compound is administered from 1 to 3 times per day.

14. A method for the treatment of a non-alcoholic convulsive seizure, comprising administering to a subject in need thereof a therapeutically effective amount of a compound selected from the group consisting of
(E)-3,7,11-trimethyldodeca-1,6,10-trien-3-ol,
(2E,6E)-3,7,11-trimethyldodeca-2,6,10-trien-1-amine,
(E)-3-(3,7-dimethylocta-2,6-dienyloxy)phenol, and
(2E,6E)-7,11-dimethyl-3-(trifluoromethyl)dodeca-2,6,10-trien-1-ol,
or a pharmaceutically acceptable salt, ester or amide of said compound.

15. The method of claim 14, wherein the compound is (E)-3,7,11-trimethyldodeca-1,6,10-trien-3-ol.

16. The method of claim 14, wherein the compound is (2E,6E)-3,7,11-trimethyldodeca-2,6,10-trien-1-amine.

17. The method of claim 14, wherein the compound is (E)-3-(3,7-dimethylocta-2,6-dienyloxy)phenol.

18. The method of claim 14, wherein the compound is (2E,6E)-7,11-dimethyl-3-(trifluoromethyl)dodeca-2,6,10-trien-1-ol.

19. The method of claim 14 wherein the non-alcoholic convulsive seizure is selected from the group consisting of: generalized epileptic seizures; absence seizures, myoclonic seizures; clonic seizures; tonic seizures; tonic-clonic seizures; atonic seizures; pseudoepileptic or non-epileptic seizures caused by cardiovascular disease, toxic or metabolic disorders including hypoglycemia and drug toxicity, or sleep disorders; non-epileptic seizures induced by psychiatric conditions including hysteria and schizophrenia; convulsions or seizures caused by acquired immunodeficiency syndrome (AIDS), Parkinson's disease, Alzheimer's disease, other degenerative disease including Huntington's chorea, schizophrenia, obsessive compulsive disorders, tinnitus, neuralgia, trigeminal neuralgia, post-traumatic epilepsy, intoxication or withdrawal from barbiturates, brain illness or injury, brain tumor, choking, drug abuse, electric shock, fever, head injury, heart disease, heat illness, high blood pressure, meningitis, poisoning, stroke, toxemia of pregnancy, uremia related to kidney failure, venomous bites and stings, withdrawal from benzodiazepines, febrile convulsions, and afebrile infantile convulsions.

20. The method of claim 14 wherein the convulsive seizure is a partial or generalized epileptic seizure.

21. The method of claim 14 wherein the subject is human.

* * * * *

UNITED STATES PATENT AND TRADEMARK OFFICE
CERTIFICATE OF CORRECTION

| | |
|---|---|
| PATENT NO. | : 10,201,510 B2 |
| APPLICATION NO. | : 11/815513 |
| DATED | : February 12, 2019 |
| INVENTOR(S) | : Jean-Baptiste Roullet, John C. Crabbe, Jr. and Pamela Metten |

It is certified that error appears in the above-identified patent and that said Letters Patent is hereby corrected as shown below:

In the Specification

Column 1, Line 37, please insert the following:
--ACKNOWLEDGEMENT OF GOVERNMENT SUPPORT
This work was supported by the U.S Department of Veterans Affairs and the Federal Government has certain rights to this invention.--

Signed and Sealed this
Fourth Day of July, 2023

*Katherine Kelly Vidal*

Katherine Kelly Vidal
*Director of the United States Patent and Trademark Office*